United States Patent
Chabrecek et al.

(10) Patent No.: US 6,468,667 B1
(45) Date of Patent: Oct. 22, 2002

(54) OPHTHALMIC MOLDING

(75) Inventors: Peter Chabrecek, Riehen; Dieter Lohmann, Münchenstein; Markus Streiff, Birsfelden, all of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/609,493

(22) Filed: Jun. 30, 2000

(30) Foreign Application Priority Data

Jun. 30, 1999 (EP) .............................................. 99112426

(51) Int. Cl.[7] .......................... B32B 29/00; B05D 3/00; B05D 3/04; B05D 3/10; B05D 5/00; A61F 2/16
(52) U.S. Cl. ...................... 428/532; 427/2.24; 427/337; 427/338; 427/399; 623/6.62
(58) Field of Search ..................... 428/532; 427/2.24, 427/338, 337, 339; 623/6.62

(56) References Cited

U.S. PATENT DOCUMENTS

| | | |
|---|---|---|
| 4,940,751 A | 7/1990 | Frances et al. ............ 525/54.2 |
| 5,571,882 A | 11/1996 | Vetter ...................... 526/238.2 |
| 5,652,014 A * | 7/1997 | Galin et al. ................ 427/2.24 |
| 5,759,823 A | 6/1998 | Wong ........................... 435/97 |
| 5,879,912 A * | 3/1999 | Roth ........................... 435/72 |
| 6,106,554 A * | 8/2000 | Bretton ...................... 623/6.62 |

FOREIGN PATENT DOCUMENTS

| WO | WO 95/24497 | 9/1995 |
| WO | WO 98/28026 | 7/1998 |

OTHER PUBLICATIONS

Sintov et al, Biomaterials (1993), 14(7), 483–90.*

* cited by examiner

*Primary Examiner*—Michael Barr
*Assistant Examiner*—Elena Tsoy
(74) *Attorney, Agent, or Firm*—R. Scott Meece; Jian S. Zhou; Richard I. Gearhart

(57) ABSTRACT

The invention relates to an ophthalmic molding such as a contact lens or any kind of ocular prostheses comprising an organic bulk material having covalently bonded to its surface an acceptor saccharide to which is enzymatically attached one or more further carbohydrates. The ophthalmic moldings of the invention have desirable characteristics regarding, for example, adherence to the substrate, durability, hydrophilicity, wettability or biocompatibility.

8 Claims, No Drawings

OPHTHALMIC MOLDING

BACKGROUND OF THE INVENTION

Biological systems usually expose a number of particular carbohydrates on those of their surfaces which are in contact with biological fluids, cells and tissues. Biocompatibility, bioadhesion, cell accumulation, molecular recognition, cell attachment, water retention, lubrication or defense against microbial attack are among the important functions which are thus controlled by the pattern of surface carbohydrates.

Synthetic bulk materials used for the manufacture of ophthalmic moldings in general lack the sufficient biocompatibility and affinity to maintain growth and permanent anchoring of healthy epithelial cells on their surface. A variety of different types of surface modifications has been proposed in the prior art to overcome this problem. However, the known surface coatings often do not provide the desired coating characteristics, for example cell growth ability or the ability to hold a continuous layer of an aqueous solution, e.g. human body fluids such as tears or mucus layers, for a prolonged period of time.

SUMMARY OF THE INVENTION

Surprisingly, it now has been found that the drawbacks of known bulk materials used for the manufacture of ophthalmic moldings may be overcome by covalently linking to the material surface specific carbohydrates which mimic a biological surface appropriate for cell attachment and, especially in case of contact lenses, provide high wettability, lubricity, water retention, on-eye comfort as well as long-term deposit resistance, microbial resistance and favorable lens movement on the eye.

The present invention therefore in one aspect relates to an ophthalmic molding comprising an organic bulk material having covalently bonded to its surface an acceptor saccharide to which is enzymatically attached one or more further carbohydrates selected from the group consisting of galactose, mannose, fucose, galactosamine, N-acetyl galactosamine, N-acetyl glucosamine, ialic acid and an oligosaccharide comprising one or more of the aforementioned arbohydrates.

Examples of suitable organic bulk materials are natural or synthetic organic polymers, for example polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); elastomers (silicones, polybutadiene and polyisoprene); or modified or unmodified biopolymers (collagen, cellulose, chitosan and the like).

DETAILED DESCRIPTION OF THE PREFERRED EMBODIMENTS

A preferred group of organic bulk materials are those being conventionally used for the manufacture of ophthalmic devices which are not hydrophilic per se. Such materials are known to the skilled artisan and may comprise for example polysiloxanes, perfluoroalkylpolyethers, fluorinated poly(meth)acrylates or equivalent fluorinated polymers derived e.g. from other polymerizable carboxylic acids, polyalkyl(meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of organic bulk materials are those being conventionally used for the manufacture of ophthalmic devices which are derived from one or more different ethylenically unsaturated monomers comprising a hydrophilic group, for example a carboxy, carbamoyl, sulfate, sulfonate, phosphate, amine, ammonium, acetate or hydroxy group. The hydrophilic groups are inherently present in the bulk material and therefore also at the surface of a ophthalmic device manufactured therefrom. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol or copolymers for example from two or more monomers from the group hydroxyethyl acrylate, hydroxyethyl methacrylate, N-vinyl pyrrolidone, acrylic acid, methacrylic acid, acrylamide, dimethyl acrylamide, vinyl alcohol and the like. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

Still another group of preferred organic bulk materials are amphiphilic segmented copolymers comprising at least one hydrophobic segment, for example a polydimethylsiloxane or perfluoroalkylpolyether segment, and at least one hydrophilic segment, for example a polyoxyalkylene, poly(vinylpyrrolidone), polyhydroxyalkylacrylate or -methacrylate, polyacyl alkylene imine, polyacryl amide, polyvinyl alcohol, polyvinyl ether or polyol segment, which are linked through a direct bond or a bridge member. Examples are silicone hydrogels, for example those disclosed in PCT applications WO 96/31792 and WO 97/49740 which are herewith incorporated by reference.

Suitable acceptor saccharides comprise mono- or oligosaccharides or suitable derivatives thereof. Throughout this application the term oligosaccharide is to be understood as meaning a carbohydrate having, for example, from 2 to 20 and preferably from 2 to 10 saccharide units. The oligosaccharide may be a linear or a branched oligosaccharide. A suitable derivative of a mono- or oligosaccharide is, for example, a respective carbohydrate which is substituted by carboxy, sulfo, sulfato, thiol, amino or N—$C_1$–$C_4$-alkanoylamino such as acetylamino, or a suitable salt thereof, or is a carbohydrate comprising a desoxyhexose.

The acceptor saccharide is preferably a mono-, di- or tri- or tetrasaccharide which in case of an oligosaccharide may be linear or branched. In one embodiment of the invention the acceptor saccharide is a mono- or disaccharide and in particular a disaccharide. Examples of preferred acceptor saccharides are thus mannose, lactose, lactobionic acid, N-acetyl lactosamine, galactose, N-acetyl galactosamine and N-acetyl glucosamine and in particular lactose, lactobionic acid, N-acetyl lactosamine or N-acetylgalactosamine. In a further embodiment of the invention the acceptor saccharide is a tetrasaccharide, in particular a branched tetrasaccharide.

The carbohydrate to be enzymatically attached to the acceptor saccharide may be one of the afore-mentioned monosaccharides or an oligosaccharide comprising at least one of said monosaccharides, for example an oligomannoside. It is preferred to enzymatically attach an afore-mentioned monosaccharide which may have any possible stereochemical configuration and preferably has the stereochemical configuration of its natural occurrence. The attachment of galactosamine or sialic acid includes suitable salts thereof. Preferably sialic acid is enzymatically attached to the acceptor saccharide. A further preferred embodiment of the invention comprises the enzymatical attachment of two or more of the afore-mentioned monosaccharides to the acceptor carbohydrate.

The covalent bonding of the acceptor saccharide to the bulk material surface may occur according to any convenient method that is known in the prior art.

According to one embodiment of the invention the ophthalmic moldings may comprise (a) a bulk material carrying reactive groups on its surface and (b) a surface coating obtainable by reacting the reactive groups of the bulk material surface with a functional group of the acceptor saccharide and before or after said covalent bonding of the acceptor saccharide to the bulk material enzymatically attaching the further carbohydrate(s) to the acceptor saccharide.

According to this embodiment the reactive groups on the surface of the bulk material may be reacted directly with a functional group of the acceptor saccharide which is co-reactive with the reactive groups of the bulk material, or, preferably, the acceptor saccharide is linked to the bulk material carrying reactive groups via a divalent organic spacer.

According to another embodiment of the invention, the ophthalmic moldings may comprise (a) a bulk material having covalently bonded to its surface initiator moieties for radical polymerization; and (b) a surface coating obtainable by grafts polymerizing one or more different acceptor saccharides comprising an ethylenically unsaturated double bond onto the bulk material surface provided with the initiator radicals and before or after said grafts polymerization enzymatically attaching the further carbohydrate(s) to the acceptor saccharide.

Suitable functional groups may be inherently (a priori) present at the surface of the bulk material. If substrates contain too few or no reactive groups, the bulk material surface can be modified by methods known per se, for example plasma chemical methods (see, for example, WO 94/06485 or WO 98/28026), or conventional functionalization with groups such as —OH, —NH$_2$ or —CO$_2$H produced. Suitable functional groups may be selected from a wide variety of groups well known to the skilled artisan. Typical examples are e.g. hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. Preferred reactive groups on the bulk material surface are amino, hydroxy, isocyanato, isothiocyanato, glycidyl, anhydride, lactone and azlactone, in particular amino, isocyanato, glycidyl and azlactone.

One group of preferred bulk materials carrying reactive groups are bulk materials having hydroxy or in particular amino groups on their surface. Another group of preferred bulk materials carrying reactive groups concerns bulk materials which are coated with a primary polymeric coating carrying reactive groups predominantly on its surface. These primary polymeric coatings on the bulk material surface may be obtained, for example, by polymerizing an ethylenically unsaturated compound carrying a reactive group on the bulk material surface. Suitable ethylenically unsaturated compounds for this purpose are, for example, ethylenically unsaturated compounds carrying a carboxy, glycidyl, isocyanato, isothiocyanato, carboxy anhydride, lactone or azlactone group. Examples of specific unsaturated compounds carrying a reactive group are 2-isocyanatoethyl methacrylate, glycidyl methacrylate, acrylic acid anhydride, methacrylic acid anhydride or 2-vinyl-4,4-dimethyl-azlactone. Particulars concerning the preparation of a primary polymeric coating carrying reactive groups on a bulk material surface and its properties may be taken from WO 98/28026 which is herewith incorporated by reference. In case that the acceptor saccharide is linked to the bulk material surface directly or via a spacer, this may be performed, for example, by reacting the reactive groups of an organic bulk material surface as mentioned above with a compound of formula

$$X_1—(R_1—X_2)_u—(saccharide) \quad (1),$$

wherein R$_1$ is a divalent organic radical having from 2 to 30 C-atoms which may be further substituted, (saccharide) is the radical of an above-mentioned acceptor saccharide or a derivative thereof, X$_1$ is a functional group that is co-reactive to the reactive groups on the organic bulk material surface, X$_2$ is a functional group linking R$_1$ to the acceptor saccharide radical (saccharide), and u is the number 0 or 1.

(saccharide) denotes the radical of an acceptor saccharide or a derivative thereof as mentioned above. In some cases it may be appropriate to protect a part of the hydroxy groups of the acceptor saccharide, for example, by acetylation or benzoylation, before attaching it to the bulk material surface and removing the protective groups afterwards. Suitable methods of adding and removing protective groups to/from a carbohydrate are known to the art-skilled worker in the field of carbohydrate chemistry.

Examples of a suitable radicals R$_1$ are linear or branched C$_2$–C$_{30}$-alkylene which is unsubstituted or substituted, for example, by hydroxy, and is uninterrupted or interrupted, for example, by —O—, —NR— or —C(O)NH— wherein R is hydrogen or C$_1$–C$_4$-alkyl; C$_1$–C$_{12}$-alkylene-C$_6$–C$_{10}$-arylen or C$_1$–C$_{12}$-alkylene-C$_6$–C$_{10}$-arylen-C$_1$–C$_{12}$-alkylene, for example C$_1$–C$_{12}$-alkylene-phenylene or C$_1$–C$_{12}$-alkylene-phenylene-C$_1$–C$_{12}$-alkylene; C$_1$–C$_{12}$-alkylene-C$_5$–C$_{10}$-cycloalkylene, for example C$_1$–C$_{12}$-alkylene-cyclohexylene or isophoronyl; C$_1$–C$_{12}$-alkylene-C$_5$–C$_{10}$-cycloalkylene-C$_1$–C$_{12}$-alkylene, for example C$_1$–C$_{12}$-alkylene-cyclohexylene-C$_1$–C$_{12}$-alkylene; or C$_1$–C$_{12}$-alkylene-heterocyclene or C$_1$–C$_{12}$-alkylene-heterocyclene-C$_1$–C$_{12}$-alkylene, wherein the heterocyclyl ring is each, for example, five- or six-membered, contains at least one N-, O- or S-atom and in addition may comprise one or more carbonyl groups, for example C$_1$–C$_{12}$-alkylene-succinimidylene or N,N-di-C$_1$–C$_{12}$-alkylene-piperazinylene.

R$_1$ is advantageously linear or branched C$_2$–C$_{24}$-alkylene or C$_1$–C$_{12}$-alkylene-C$_5$–C$_{10}$-cycloalkylene, preferably linear or branched C$_4$–C$_{18}$-alkylene and most preferably linear C$_6$–C$_{10}$-alkylene, which in each case may be interrupted by —O—, —NR— or —C(O)NH—. The divalent organic spacer is most preferably a linear $C_2$-$C_{10}$ alkylene radical which is uninterrupted H—or interrupted by —O—.

$X_2$ is, for example a group —C(O)O—, —OC(O)—, —C(O)NR—, —NRC(O)—, —OC(O)NH—, —NHC(O)O—, —NHC(S)NH— or —NHC(O)NH—, and is preferably a radical —NHC(O)—, —NHC(O)O— or —C(O)O—, wherein R is hydrogen or $C_1$-$C_4$-alkyl, and the left bond is each directed to $R_1$ and the right bond is directed to the acceptor saccharide.

$X_1$ is, for example, hydroxy, amino, isocyanato, isothiocyanato, carboxy or a carboxy derivative, for example a carboxy anhydride, ester, halogenid or lactone, and is preferably hydroxy, amino or isocyanato.

The variable u is an integer of 0 or preferably of 1. R is preferably hydrogen.

The compounds of formula (1) are known or may be prepared according to methods known in the art. Likewise, the reactions of a compound of formula (1) with the organic bulk material surface comprising reactive groups are well-known in the art and may be carried out as described in textbooks of organic chemistry.

According to a further embodiment of the invention the bulk material comprises covalently bonded to its surface initiator radicals for radical polymerization and a derivative of the acceptor saccharide comprising an ethylenically unsaturated double bond is grafts polymerized onto the bulk material surface provided with the initiator radicals.

Polymerization initiators bonded on the surface of the bulk material are typically those that are initiating a radical polymerization of ethylenically unsaturated compounds. The radical polymerization may be induced thermally, or preferably by irradiation.

Suitable thermal polymerization initiators are known to the skilled artisan and comprise for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis (isobutyronitrile), 1,1'-azo-bis (1-cyclohexanecarbonitrile), 2,2'-azo-bis(2,4-dimethylvaleronitrile) and the like. The thermal initiators may be linked to the surface of the bulk material by methods known per se, for example as disclosed in EP-A-0378511.

Initiators for the radiation-induced polymerization are particularly functional photoinitiators having a photoinitiator part and in addition a functional group that is coreactive with functional groups of the substrate, particularly with —OH, —SH, —NH$_2$, epoxy, carboxanhydride, alkylamino,—COOH or isocyanato groups. The photoinitiator part may belong to different types, for example to the thioxanthone type and preferably to the benzoin type. Suitable functional groups that are coreactive with the surface of the bulk material are for example a carboxy, hydroxy, epoxy or isocyanato group.

Preferred polymerization initiators for use in the present invention are the photoinitiators of formulae (I) and (Ia) as disclosed in U.S. Pat. No. 5,527,925, those of the formula (I) as disclosed in PCT application WO 96/20919, or those of formulae II and III including formulae IIa–IIy and IIg as disclosed in EP-A-0281941, particularly formulae IIb, IIi, IIm, IIn, IIp, IIr, IIs, IIx and IIIg therein. The respective portion of said three documents including the definitions and preferences given for the variables in said formulae are herewith included by reference.

The polymerization initiator moieties are preferably derived from a functional photoinitiator of the formula

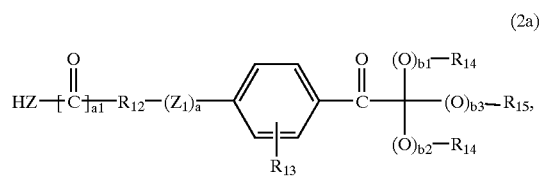

(2a)

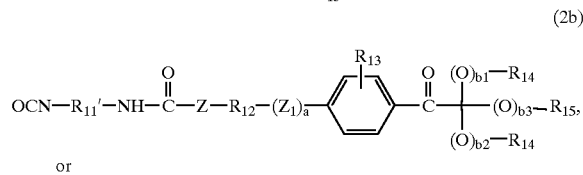

(2b)

or

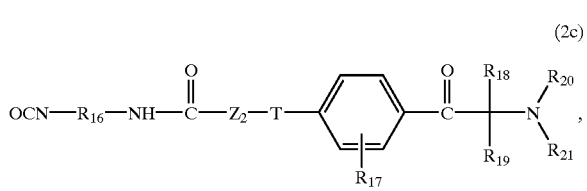

(2c)

wherein Z is bivalent —O—, —NH— or —NR$_{22}$-; $Z_1$ is —O—, —O—(O)C—, —C(O)—O— or —O—C(O)—O—; $R_{13}$ is H, $C_1$-$C_{12}$-alkyl, $C_1$-$C_{12}$-alkoxy or N-$C_1$-$C_{12}$-alkylamino; $R_{14}$ and $R_{15}$ are each independently of the other H, linear or branched $C_1$-$C_8$-alkyl, $C_1$-$C_8$-hydroxyalkyl or $C_6$-$C_{10}$-aryl, or the groups $R_{14}$—(O)$_{b1}$— and $R_{14}$—(O)$_{b2}$— together are —(CH$_2$)$_c$— wherein c is an integer from 3 to 5, or the groups $R_{14}$—(O)$_{b1}$—, $R_{14}$—(O)b$_2$— and $R_{15}$—(O$_1$)$_{b3}$— together are a radical of the formula

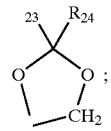

$R_{12}$ is a direct bond or linear or branched $C_1$-$C_8$-alkylene that is unsubstituted or substituted by —OH and/or is uninterrupted or interrupted by one or more groups —O—, —O—C(O)— or —O—C(O)—O—; $R_{11}$' is branched $C_3$-$C_{18}$-alkylene, unsubstituted or $C_1$-$C_4$-alkyl- or $C_1$-$C_4$-alkoxy-substituted $C_6$-$C_{10}$-arylene, or unsubstituted or $C_1$-$C_4$-alkyl- or $C_1$-$C_4$-alkoxy-substituted $C_7$-$C_{18}$-aralkylene, unsubstituted or $C_1$-$C_4$-alkyl- or $C_1$-$C_4$-alkoxy-substituted $C_3$-$C_8$-cycloalkylene, unsubstituted or $C_1$-$C_4$-alkyl- or $C_1$-$C_4$-alkoxy-substituted $C_3$-$C_8$-cycloalkylene-$C_yH_{2y}$— or unsubstituted or $C_1$-$C_4$-alkyl- or $C_1$-$C_4$-alkoxy-substituted —$C_yH_{2y}$—($C_3$-$C_8$-cycloalkylene)—$C_yH_{2y}$— wherein y is an integer from 1 to 6; $R_{16}$ independently has the same definitions as $R_{11}$' or is linear $C_3$-$C_{18}$-alkylene; $R_{22}$ is linear or branched $C_1$-$C_6$-alkyl; T is bivalent —O—, —NH—, —S—, $C_1$-$C_8$-alkylene or

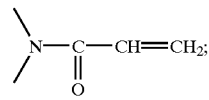

$Z_2$ is a direct bond or —O—(CH$_2$)$_d$— wherein d is an integer from 1 to 6 and the terminal CH$_2$ group of which is linked to the adjacent T in formula (2c); $R_{17}$ is H, $C_1$-$C_{12}$-alkyl, $C_1$-$C_{12}$-alkoxy, N—$C_1$-$C_{12}$- alkylamino or —NR$_{25}$R$_{26}$ wherein R$_{25}$ is C$_1$–C$_8$-alkyl and R$_{26}$ is H or C$_1$–C$_8$-alkyl; R$_{18}$ is linear or branched C$_1$–C$_8$-alkyl, C$_2$–C$_8$-alkenyl or C$_6$–C$_{10}$-aryl-C$_1$–C$_8$-alkyl; R$_{19}$ independently of R$_{18}$ has the same definitions as R$_{18}$ or is C$_6$–C$_{10}$-aryl, or R$_{18}$ and R$_{19}$ together are —(CH$_2$)$_e$— wherein e is an integer from 2 to 6; R$_{20}$ and R$_2$, are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{20}$ and R$_{21}$ together are —(CH$_2$)$_{f1}$—Z$_3$—(CH$_2$)$_{f2}$— wherein Z$_3$ is —S— or —NR$_{26}$—, and R$_{26}$ is H or C$_1$–C$_8$-alkyl and f1 and f2 are each independently of the other an integer from 2 to 4; R$_{23}$ and R$_{24}$ are each independently of the other H, C$_1$–C$_8$-alkyl, C$_3$–C$_8$-cycloalkyl, benzyl or phenyl; and a, a1, b1, b2 and b3 are each independently of the other 0 or 1; subject to the provisos that b1 and b2 are each 0 when R$_{15}$ is H; that the total of (b1+b2+b3) is not exceeding 2; and that a is 0 when R$_{12}$ is a direct bond.

A preferred sub-group of compounds of formula (2a) or (2b) comprises those wherein, b1 and b2 are each 0; Z and Z$_1$ are each bivalent —O—; b3 is 0 or 1; R$_{14}$ is C$_1$–C$_4$-alkyl or phenyl, or both groups R$_{14}$ together are tetramethylene or pentamethylene; R$_{15}$ is C$_1$–C$_4$-alkyl or H, R$_{13}$ is hydrogen; a and a1 are each independently 0 or 1; R$_{12}$ is linear or branched C$_2$–C$_4$-alkylene, or is a direct bond, in which case a is 0; R$_{11}$' is branched C$_1$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-C$_y$H$_{2y}$— or —C$_y$H$_{2y}$-cyclohexyl-C$_y$H$_{2y}$— or cyclohexyl-C$_y$H$_{2y}$— or —C$_y$H$_{2y}$-cyclohexyl-C$_y$H$_{2y}$— substituted by from 1 to 3 methyl groups; y is 1 or 2; and R$_{16}$ has the same definitions as R$_{11}$' or is linear C$_3$–C$_{10}$alkylene.

An especially preferred sub-group of compounds of formula (2a) or (2b) comprises those wherein, b1 and b2 are each 0, Z and Z$_1$ are each bivalent —O—, b3 is 0 or 1; R$_{14}$ is methyl or phenyl, or both groups R$_{14}$ together are pentamethylene; R$_{15}$ is methyl or H; R$_{13}$ is hydrogen; a is 1 and R$_{12}$ is ethylene, or a is 0 and R$_{12}$ is a direct bond; a1 is 0 or 1; R$_{11}$' is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-CH$_2$— or cyclohexyl-CH$_2$— substituted by from 1 to 3 methyl groups; R$_{16}$ has the same definitions as R$_{11}$' or is linear C$_5$–C$_{10}$alkylene.

A preferred sub-group of compounds of formula (2c) comprises those wherein T is bivalent —O—, —NH—, —S— or —(CH$_2$)y— wherein y is an integer from 1 to 6; Z$_2$ is a direct bond or —O—(CH$_2$)y— wherein y is an integer from 1 to 6 and the terminal CH$_2$ group of which is linked to the adjacent T in formula (2c); R$_{17}$ is H, C$_1$–C$_{12}$-alkyl or C$_1$–C$_{12}$-alkoxy; R$_{18}$ is linear C$_1$–C$_8$-alkenyl or C$_6$–C$_{10}$-aryl-C$_1$–C$_8$-alkyl; R$_{19}$ independently of R$_{18}$ has the same definitions as R$_{18}$ or is C$_6$–C$_{10}$-aryl, or R$_{18}$ and R$_{19}$ together are —(CH$_2$)e— wherein e is an integer from 2 to 6; R$_{20}$ and R$_{21}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{20}$ and R$_{21}$ (CH$_2$)$_{f2}$— wherein Z$_3$ is a direct bond, —O—, —S— or —NR$_{26}$—, and R$_{26}$ is H or C$_1$–C$_8$-alkyl and f1 and F2 are each independently of the other an integer from 2 to 4; and R$_{16}$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$— or cyclohexylene-CH$_2$-substituted by from 1 to 3 methyl groups.

An especially preferred sub-group of compounds of formula (2c) comprises those wherein T is bivalent —O—; Z$_2$ is —O—(CH$_2$)$_y$— wherein y is an integer from 1 to 4 and the terminal CH$_2$ group of which is linked to the adjacent T in formula (2c); R$_{17}$ is H; R$_{18}$ is methyl, alkyl, tolylmethyl or benzyl, R$_{19}$ is methyl, ethyl, benzyl or phenyl, or R$_{18}$ and R$_{19}$ together are pentamethylene, R$_{20}$ and R$_2$, are each independently of the other C$_1$–C$_4$-alkyl or R$_{20}$ and R$_{21}$ together are —CH$_2$CH$_2$OCH$_2$CH$_2$—, and R$_{16}$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$— or cyclohexylene-CH$_2$-substituted by from 1 to 3 methyl groups.

Some examples of especially preferred functional photoinitiators are the compounds of formulae

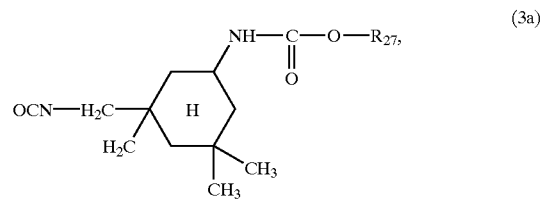

(3a)

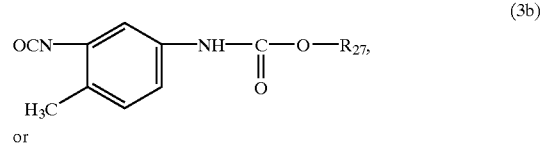

(3b)

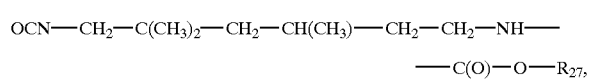

wherein R$_{27}$ is a radical

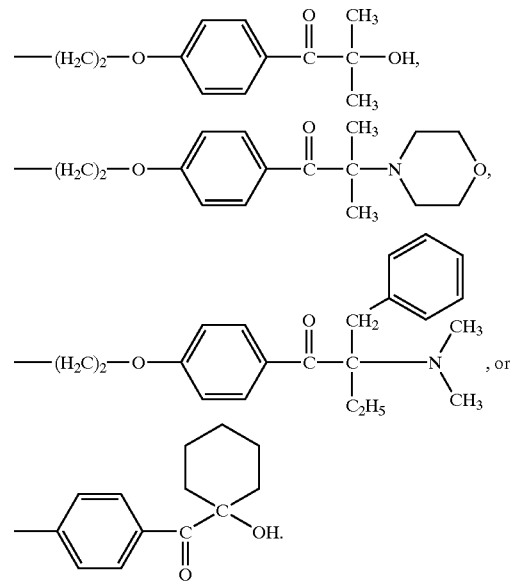

In a preferred embodiment of the invention, the covalent bonding between the organic bulk material and the photoinitiator occurs via reaction of a hydroxy, amino, alkylamino, thiol or carboxy group, particularly of a hydroxy or amino group, of the substrate surface with an isocyanato group of the photoinitiator, for example using a photoinitiator of the above formula (2b), (2c), (3a), (3b) or (3c). Suitable methods for this are known, for example, from the above-mentioned documents. The reaction may be carried out, for example, at elevated temperature, for example from 0° to 100° C. and preferably at room temperature, and optionally in the presence of a catalyst. After the reaction, excess compounds can be removed, for example, with solvents.

According to a preferred embodiment of the invention the organic bulk material is an organic polymer containing H-active groups, in particular —OH, —NH$_2$ and/or —NH—, on the surface that are coreactive with isocyanato groups, some or all of whose H atoms have been substituted by radicals of the formulae

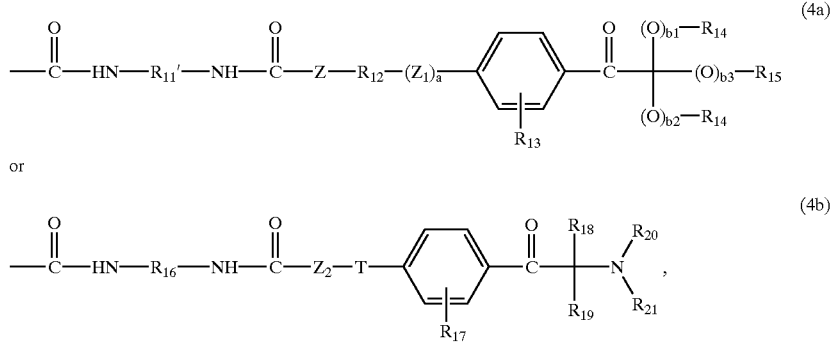

wherein for the variables $R_{11}'$–$R_{21}$, T, Z, $Z_1$, $Z_2$, a, b1, b2 and b3 the above-given meanings and preferences apply.

In another preferred embodiment of the invention, the covalent bonding between the organic bulk material and the photoinitiator occurs via reaction of a epoxy, carboxanhydride, lactone, azlactone or preferably isocyanato group of the substrate surface with a hydroxy, amino, alkylamino, thiol or carboxy group, particularly with a carboxy, hydroxy or amino group, of the photoinitiator, for example using a photoinitiator of the above formula (2a). This may be carried out, for example, by first reacting an above-mentioned bulk material containing H-active groups on the surface, in particular —OH, —NH$_2$ and/or —NH, selectively with one isocyanato group of a m diisocyanate of formula OCN—$R_{11}'$—NCO, wherein $R_{11}'$ has the above-given meanings, and then reacting the modified bulk material with a photoinitiator of the above-mentioned formula (2a).

Suitable derivatives of an acceptor saccharide comprising an ethylenically unsaturated double bond are, for example, those of formula

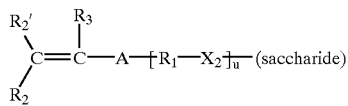

(5)

wherein A is a radical of formula

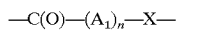 (6a) or

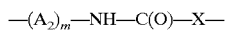 (6b); or

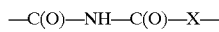 (6c);

$R_2$ is hydrogen, $C_1$–$C_6$-alkyl or a radical —COOR';

$R_3$, $R^1$ and $R_2'$ are each independently of the other hydrogen or $C_1$–$C_6$-alkyl;

$A_1$ is —O—$C_2$–$C_{12}$-alkylene which is unsubstituted or substituted by hydroxy, or is —O—$C_2$–$C_{12}$-alkylene—NH—C(O)— or —O—$C_2$–$C_{12}$-alkylene—O—C(O)—NH—$R_{11}$—NH—C(O)—, wherein $R_{11}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X is a bivalent group —O— or —NR", wherein R" is hydrogen or $C_1$–$C_6$-alkyl; and $R_1$, $X_2$, u and (saccharide) are each as defined above.

The following preferences apply to the variables contained in the definition of the macromonomer of formula (5):

$R^1$ is preferably hydrogen or $C_1$–$C_4$-alkyl, more preferably hydrogen or $C_1$–$C_2$-alkyl and particularly preferably hydrogen.

$R_2$ is preferably hydrogen, methyl or carboxyl, and particularly preferably hydrogen.

$R_2'$ is preferably hydrogen or methyl and particularly preferably hydrogen.

$R_3$ is preferably hydrogen or methyl.

X is preferably a bivalent group —O— or —NH— and in particular a bivalent group —O—.

The radical $R_{11}$ has a symmetrical or, preferably, an asymmetrical structure. A preferred group of radicals $R_{11}$ comprises those, wherein $R_{11}$ is linear or branched $C_6$–$C_{10}$alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{11}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene—NH—C(O)— and particularly —O—$(CH_2)_{2-4}$—, —O—$CH_2$—CH(OH)—$CH_2$— or radical —O—$(CH_2)_{2-4}$—NH—C(O)—. A particularly preferred meaning of $A_1$ is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene.

n is an integer of 0 or preferably 1. m is preferably an integer of 1.

Regarding the variables $R_1$, $X_2$, u and (saccharide), each the above-given meanings and preferences apply.

A preferred group of ethylenically unsaturated acceptor saccharides according to the invention comprises compounds of the above formula (5), wherein $R_3$ is hydrogen or methyl, $R_2$ is hydrogen, methyl or carboxyl, $R_2'$ is hydrogen, A is a radical of the formula (6a) or (6b), $R_1$ is linear or branched $C_2$–$C_{24}$-alkylene, uninterrupted or interrupted by —O—, —NR— or —C(O)NH—, $X_2$ is a radical —C(O)O—, —NR—, —OC(O)—, —C(O)NR—, —NRC(O)—, —OC(O)NH—, —NHC(O)O—, —NHC(S)NH— or —NHC(O)NH—, R is each independently hydrogen or $C_1$–$C_4$-alkyl, u is the number 0 or 1, and (saccharide) is the radical of a mono-, di-, tri- or tetrasaccharide. An even more preferred group of ethylenically unsaturated acceptor saccharides comprises compounds of the above formula (5), wherein $R_3$ is hydrogen or methyl, $R_2$ and $R_2'$ are each hydrogen, A is a radical of the formula (6a), u is the number 1, $R_1$ is linear $C_2$–$C_{10}$ alkylene radical which is uninterrupted or interrupted by —O—, $X_2$ is a radical —NHC(O)—, —NHC(O)O— or —C(O)O—, and (saccharide) is the radical of a disaccharide.

The acceptor saccharide derivatives of formula (5) may be prepared by methods known per se. For example, the compounds of formula (5) are obtainable by reacting a compound of formula

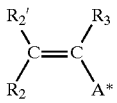 (7)

wherein $R_2$, $R_2'$ and $R_3$ each have the above-given meaning and A* is, for example, a group —C(O)—A, wherein A is halogen, particularly chlorine, an ester group an oxyalkylene radical comprising an epoxy group, for example the radical

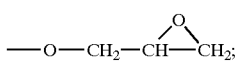

or is a radical —O—)$C_2$–$C_{12}$-alkylene-N=C=O; or A* is a radical —$(A_2)_m$—N=C=O, wherein $A_2$ and m have the above-given meaning, with a compound of formula HX—$(R_1$—$X_2)_u$—(saccharide)   (8), wherein $R_1$, $X_1$ $X_2$, u and (saccharide) each have the above-given meaning.

The reactions of a compound of formula (7) having a carboxylic acid halide group, an epoxy group or an isocyanato group with an amino or hydroxy compound of formula (8) are well-known in the art and may be carried out as described in textbooks of organic chemistry. For example, the reaction of an isocyanato derivative of formula (7) with a compound of formula (8) may be carried out in an inert organic solvent such as an optionally halogenated hydrocarbon, for example petrolium ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of an isocyanato derivative of formula (7) with a compound of formula (8) wherein —XH is an amino group also may be carried out in an aqueous solution in the absence of a catalyst. It is advantageous to carry out the above reactions under an inert atmosphere, for example under an nitrogen or argon atmosphere.

The derivatives of the acceptor saccharide comprising an ethylenically unsaturated double bond, for example, of formula (5) may be applied to the initiator-modified bulk material surface and polymerized there according to processes known per se. For example, the bulk material is immersed in a solution of the double bond modified acceptor saccharide, or a layer of the double bond modified acceptor saccharide is first of all deposited on the modified bulk material surface, or example, by dipping, spraying, spreading, knife coating, pouring, rolling, spin coating or vacuum vapor deposition. The polymerization of the modified acceptor saccharide on the bulk material surface then may be initiated, for example, thermally by the action of heat or preferably by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend for example on the desired properties of the resulting composite material but is usually in the range of up to 30 minutes, preferably from 10 seconds to 10 minutes, and particularly preferably from 0.5 to 5 minutes. It is advantageous to carry out the irradiation in an atmosphere of inert gas. After the polymerization, any non-covalently bonded acceptor saccharide can be removed, for example by treatment with suitable solvents.

Whereas one feature of this embodiment of the invention comprises to polymerize one or more different derivatives of an acceptor saccharide comprising an ethylenically unsaturated double bond onto the surface of the ophthalmic molding as outlined above, another feature of this embodiment of the invention comprises to copolymerize one or more above-mentioned ethylenically unsaturated acceptor saccharides with one or more different hydrophilic macromonomers onto the surface.

Suitable macromonomers correspond, for example, to formula

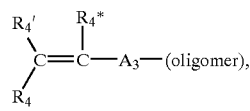 (9)

wherein $R_4$ independently has the meaning of $R_2$, $R_4'$ independently has the meaning of $R_2'$, $R_4^*$ independently has the meaning of $R_3$, $A_3$ independently has the meaning of A or is a radical of formula

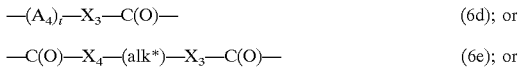

$A_3$ and $R_4$, together with the adjacent double bond, are a radical of formula

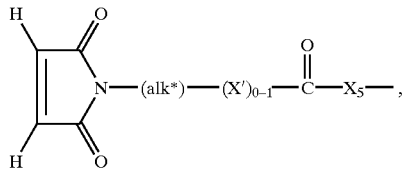

$X'$ $X_3$, $X_4$ and $X_5$ are each independently of the other a bivalent group —O— or —NR* wherein R* is hydrogen or $C_1$–$C_6$–alkyl;

$A_4$ independently has the meaning of $A_2$ above;

t is an integer of 0 or 1;

(alk*) is $C_2$–$C_{12}$-alkylene;

and (oligomer) denotes the radical of a telomer of formula

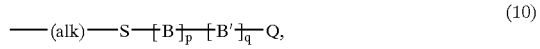

wherein (alk) is $C_2$–$C_{12}$-alkylene,

Q is a monovalent group that is suitable to act as a polymerization chain-reaction terminator, p and q are each independently of another an integer from 0 to 100, wherein the total of (p+q) is an integer from 2 to 250, and B and B' are each independently of the other a 1,2-ethylene radical derivable from a copolymerizable vinyl monomer by replacing the vinylic double bond by a single bond, at least one of the radicals B and B' being substituted by a hydrophilic substituent;

The following preferences apply to the variables contained in formulae (6d), (6e), (6f), (9) and (10):

For $R_4$ independently the meanings and preferences given above for $R_2$ apply.

For $R_4'$ independently the meanings and preferences given above for $R_2'$ apply.

For $R_4^*$ independently the meanings and preferences given above for $R_3$ apply.

For $A_4$ independently the meanings and preferences given above for $A_2$ apply.

t is preferably an integer of 1.

X' and $X_3$ are each independently preferably a group —O— or —NH— and in particular a group —NH—.

$X_4$ and $X_5$ are each independently preferably a group —O— or —NH—.

(alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

$A_3$ preferably denotes a radical of formula (6a) or (6b) given above and particularly preferably a radical of formula (6a), wherein the above given meanings and preferences apply for the variables contained therein.

A preferred group of hydrophilic macromonomers comprises compounds of the above formula (9), wherein $R_4^*$ is hydrogen or methyl, $R_4$ is hydrogen, methyl or carboxyl, $R_4'$ is hydrogen, and $A_3$ is a radical of the formula (6a) or (6b). An even more preferred group of hydrophilic macromonomers comprises compounds of the above formula (9), wherein $R_4^*$ is hydrogen or methyl, $R_4$ and $R_4'$ are each hydrogen, and $A_3$ is a radical of the formula (2a). A further group of preferred hydrophilic macromonomers comprises compounds of formula (9), wherein $A_3$ is a radical of formula (6e) above. Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50.

Suitable hydrophilic substituents of the radicals B or B' may be non-ionic, anionic, cationic or zwitterionic substituents. Accordingly, the telomer chain of formula (10) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one preferred embodiment of the invention, the telomer radical of formula (10) is composed solely of non-ionic monomer units B and/or B'. In another preferred embodiment of the invention, the telomer radical of formula (10) is composed solely of ionic monomer units B and/or B', for example solely of cationic monomer units or solely of anionic monomer units. Still another preferred embodiment of the invention is directed to telomer radicals of formula (10) comprising nonionic units B and ionic units B'.

Suitable non-ionic substituents of B or B' include for example a radical $C_1$–$C_6$-alkyl which is substituted by one or more same or different substituents selected from the group consisting of —OH, $C_1$–$C_4$-alkoxy and —$NR_9R_9'$, wherein $R_9$ and $R_9'$ are each independently of another hydrogen or unsubstituted or hydroxy-substituted $C_1$–$C_6$-alkyl or phenyl; phenyl which is substituted by hydroxy, $C_1$–$C_4$-alkoxy or —$NR_9R_9'$, wherein $R_9$ and $R_9'$ are as defined above; a radical —COOY, wherein Y is $C_1$–$C_{24}$-alkyl which is unsubstituted or substituted, for example, by hydroxy, $C_1$–$C_4$-alkoxy, —O—Si($CH_3$)$_3$, —$NR_9R_9'$ wherein $R_9$ and $R_9'$ are as defined above, a radical —O—($CH_2CH_2O$)$_{1-24}$—E wherein E is hydrogen or $C_1$–$C_6$-alkyl, or a radical —NH—C(O)—O—($CH_2CH_2O$)$_{1-24}$-E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —$CONY_1Y_2$ wherein $Y_1$ and $Y_2$ are each independently hydrogen, $C_1$–$C_{12}$-alkyl, which is unsubstituted or substituted for example by hydroxy, $C_1$–$C_4$-alkoxy or a radical —O—($CH_2CH_2O$)$_{1-24}$—E wherein E is as defined above, or $Y_1$ and $Y_2$ together with the adjacent N-atom form a five- or six-membered heterocyclic ring having no additional heteroatom or one additional oxygen or nitrogen atom; a radical —$OY_3$, wherein $Y_3$ is hydrogen; or $C_1$–$C_{12}$-alkyl which is unsubstituted or substituted by —$NR_9R_9'$; or is a radical —C(O)—$C_1$–$C_4$-alkyl; and wherein $R_9$ and $R_9'$ are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —$SO_3H$, —$OSO_3H$, —$OPO_3H_2$ and —COOH; phenyl which is substituted by one or more same or different substituents selected from the group consisting of —$SO_3H$, —COOH, —OH and —$CH_2$—$SO_3H$; —COOH; a radical —$COOY_4$, wherein $Y_4$ is $C_1$–$C_{24}$-alkyl which is substituted for example by —COOH, —$SO_3H$, —$OSO_3H$, or —$OPO_3H_2$; a radical —$CONY_5Y_6$ wherein $Y_5$ is $C_1$–$C_{24}$-alkyl which is substituted by —COOH, —$SO_3H$, —$OSO_3H$, or —$OPO_3H_2$ and $Y_6$ independently has the meaning of $Y_5$ or is hydrogen or $C_1$–$C_{12}$-alkyl; or —$SO_3H$; or a salt thereof, for example a sodium, potassium, ammonium or the like salt thereof.

Suitable cationic substituents of B or B' include $C_1$–$C_{12}$-alkyl which is substituted by a radical —$NR_9R_9'R_9''^+An^-$, wherein $R_9$, $R_9'$ and $R_9''$ are each independently of another hydrogen or unsubstituted or hydroxy-substituted $C_1$–$C_6$-alkyl or phenyl, and $An^-$ is an anion; or a radical —C(O)$OY_7$, wherein $Y_7$ is $C_1$–$C_{24}$-alkyl which is substituted by —$NR_9R_9'$, $R_9''^+An^-$ and is further unsubstituted or substituted for example by hydroxy, wherein $R_9$, $R_9'$, $R_9''$ and $An^-$ are as defined above.

Suitable zwitterionic substituents of B or B' include a radical —$R_5$—Zw, wherein $R_5$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) Non-ionic Substituents:

Preferred alkyl substituents of B or B' are $C_1$–$C_4$-alkyl, in particular $C_1$–$C_2$-alkyl, which is substituted by one or more substituents selected from the group consisting of —OH and —$NR_9R_9'$, wherein $R_9$ and $R_9'$ are each independently of another hydrogen or $C_1$–$C_4$-alkyl, preferably hydrogen, methyl or ethyl and particularly preferably hydrogen or methyl, for example —$CH_2$—$NH_2$, —$CH_2$—$N(CH_3)_2$.

Preferred phenyl substituents of B or B' are phenyl which is substituted by —$NH_2$ or $N(C_1$–$C_2$-alkyl$)_2$, for example o-, m- or p-aminophenyl.

In case that the hydrophilic substituent of B or B' is a radical —COOY, Y as optionally substituted alkyl is preferably $C_1$–$C_{12}$-alkyl, more preferably $C_1$–$C_6$-alkyl, even more preferably $C_1$–$C_4$-alkyl and particularly preferably $C_1$–$C_2$-alkyl, each of which being unsubstituted or substituted as mentioned above. In case that the alkyl radical Y is substituted by —$NR_9R_9'$, the above-given meanings and preferences apply for $R_9$ and $R_9'$. In case that the alkyl radical Y is substituted by a radical —O—$(CH_2CH_2O)_{1-24}$—E or —NH—C(O)—O—$(CH_2CH_2O)_{1-24}$—E, the number of $(CH_2CH_2O)$ units is preferably from 1 to 12 in each case and more preferably from 2 to 8. E is preferably hydrogen or $C_1$–$C_2$-alkyl.

Y as $C_5$–$C_8$-cycloalkyl is for example cyclopentyl or preferably cyclohexyl, each of which being unsubstituted or substituted for example by 1 to 3 $C_1$–$C_2$-alkyl groups. Y as $C_7$–$C_{12}$-aralkyl is for example benzyl.

Preferred nonionic radicals —COOY are those wherein Y is $C_1$–$C_6$-alkyl; or $C_2$–$C_6$-alkyl which is substituted by one or two substituents selected from the group consisting of hydroxy; $C_1$–$C_2$-alkoxy; —O—$Si(CH_3)_3$; and —$NR_9R_9'$ wherein $R_9$ and $R_9'$ are each independently of another hydrogen or $C_1$–$C_4$-alkyl; or Y is a radical —$CH_2CH_2$—O—$(CH_2CH_2O)_{1-12}$-E wherein E is hydrogen or $C_1$–$C_2$-alkyl.

More preferred non-ionic radicals —COOY are those wherein Y is $C_1$–$C_4$-alkyl; or $C_2$–$C_4$-alkyl which is substituted by one or two substituents selected from the group consisting of —OH and —$NR_9R_9'$ wherein $R_9$ and $R_9'$ are each independently of another hydrogen or $C_1$–$C_2$-alkyl; or a radical —$CH_2CH_2$—O—$(CH_2CH_2O)_{1-12}$—E wherein E is hydrogen or $C_1$–$C_2$-alkyl.

Particularly preferred radicals —COOY comprise those wherein Y is $C_1$–$C_2$-alkyl, particularly methyl; or $C_2$–$C_3$-alkyl, which is unsubstituted or substituted by hydroxy or N,N-di-$C_1$–$C_2$-alkylamino.

Preferred non-ionic substituents —C(O)—$NY_1Y_2$ of B or B' are those wherein Y1 and Y2 are each independently of the other hydrogen or $C_1$–$C_6$-alkyl which is unsubstituted or substituted by hydroxy; or $Y_1$ and $Y_2$ together with the adjacent N-atom form a heterocyclic 6-membered ring having no further heteroatom or having one further N- or O-atom. Even more preferred meanings of $Y_1$ and $Y_2$, independently of each other, are hydrogen or $C_1$–$C_4$-alkyl which is unsubstituted or substituted by hydroxy; or $Y_1$ and $Y_2$ together with the adjacent N-atom form a N—$C_1$–$C_2$-alkylpiperazino or morpholino ring. Particularly preferred non-ionic radicals —C(O)—$NY_1Y_2$ are those wherein $Y_1$ and $Y_2$ are each independently of the other hydrogen or $C_1$–$C_2$-alkyl; or $Y_1$ and $Y_2$ together with the adjacent N-atom form a morpholino ring.

Preferred non-ionic substituents —$OY_3$ of B or B' are those wherein $Y_3$ is hydrogen, $C_1$–$C_4$-alkyl which is unsubstituted or substituted by —$NH_2$ or —$N(C_1$–$C_2$-alkyl$)_2$, or is a group —C(O)$C_1$–$C_2$-alkyl. $Y_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N— or O— heteroatom, or is a 5 to 7-membered lactame. Examples of such heterocyclic radicals are N-pyrrolidonyl, 2- or 4-pyridinyl, 2-methyl pyridin-5-yl, 2-, 3- oder 4-hydroxypyridinyl N-ε-caprolactamyl, N-imidazolyl, 2-methylimidazol-1-yl, N-morpholinyl or 4-N-methylpiperazin-1-yl, particularly N-morpholinyl or N-pyrrolidonyl.

A group of preferred non-ionic substituents of B or B' comprises $C_1$–$C_2$-alkyl, which is unsubstituted or substituted by —OH or —$NR_9R_9'$, wherein $R_9$ and $R_9'$ are each independently of the other hydrogen or $C_1$–$C_2$-alkyl; a radical —COOY wherein Y is $C_1$–$C_4$-alkyl; $C_2$–$C_4$-alkyl which is substituted by —OH, —$NR_9R_9'$ wherein $R_9$ and $R_9'$ are each independently of another hydrogen or $C_1$–$C_2$-alkyl; a radical —C(O)—$NY_1Y_2$, herein $Y_1$ and $Y_2$ are each independently of the other hydrogen or $C_1$–$C_6$-alkyl which is unsubstituted or substituted by hydroxy, or $Y_1$ and Y2 together with the adjacent N-atom form a heterocyclic 6-membered ring having no further heteroatom or having one further N- or O-atom; a radical —$OY_3$, wherein $Y_3$ is hydrogen, $C_1$–$C_4$-alkyl which is unsubstituted or substituted by —$NH_2$ or —$N(C_1$–$C_2$-alkyl$)_2$, or is a group —C(O) $C_1$–$C_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino; a radical —CO—$NY_1Y_2$, wherein $Y_1$ and $Y_2$ are each independently of the other hydrogen or $C_1$–$C_4$-alkyl which is unsubstituted or substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3- oder 4- hydroxypyridinyl, N-F-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —COO—$C_1$–$C_2$-alkyl, —COO—$(CH_2)_{2-4}$—OH, —$CONH_2$, —$CON(CH_3)_2$, —CONH—$(CH_2)_2$—OH,

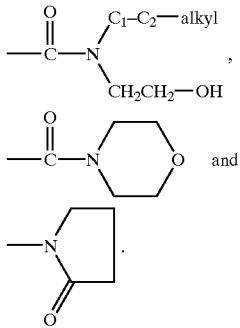

(ii) Anionic Substituents:

Preferred anionic substituents of B or B' are $C_1$–$C_4$-alkyl, in particular $C_1$–$C_2$-alkyl, which is substituted by one or more substituents selected from the group consisting of —$SO_3H$ and —$OPO_3H_2$, for example —$CH_2$—$SO_3H$; phenyl which is substituted by —$SO_3H$ or sulfomethyl, for example o-, m- or p-sulfophenyl or o-, m- or p-sulfomethylphenyl; —COOH; a radical —$COOY_4$, wherein $Y_4$ is $C_2$–$C_6$-alkyl which is substituted by —COOH, —$SO_3H$, —$OSO_3H$, —$OPO_3H_2$, in particular $C_2$–$C_4$-alkyl which is substituted by —$SO_3H$ or —$OSO_3H$; a radical —$CONY_5Y_6$ wherein $Y_5$ is $C_1$–$C_6$-alkyl substituted by sulfo, in particular $C_2$–$C_4$-alkyl substituted by sulfo, and $Y_6$ is hydrogen, for example the radical —C(O)—NH—$C(CH_3)_2$—$CH_2$—$SO_3H$; or —$SO_3H$; or a suitable salt thereof. Particular preferred anionic substituents of B or B' are —COOH, —$SO_3H$, o-, m- or p-sulfophenyl, o-, m- or p-sulfomethylphenyl or a radical —$CONY_5Y_6$ wherein $Y_5$ is $C_2$–$C_4$-alkyl substituted by sulfo, and $Y_6$ is hydrogen.

(iii) Cationic Substituents:

Preferred cationic substituents of B or B' are $C_1$–$C_4$-alkyl, in particular $C_1$–$C_2$-alkyl, which is in each case substituted by —$NR_9R_9'R_9''{}^+An^-$; or a radical —$C(O)OY_7$ wherein $Y_7$ is $C_2$–$C_6$-alkyl, in particular $C_2$–$C_4$-alkyl, which is in each case substituted by —$NR_9R_9'R_9''{}^+An^-$ and is further unsubstituted or substituted by hydroxy. $R_9$, $R_9'$ and $R_9''$ are each independently of another preferably hydrogen or $C_1$–$C_4$-alkyl, more preferably methyl or ethyl and particularly preferably methyl. Examples of suitable anions $An^-$ are $Hal^-$, wherein Hal is halogen, for example $Br^-$, $F^-$, $J^-$ or particularly $Cl^-$, furthermore $HCO_3^-$, $CO_3^{2-}$, $H_2PO_3^-$, $HPO_3^{2-}$, $PO_3^{3-}$, $HSO_4^-$, $SO_4^{2-}$ an organic acid such as $OCOCH_3^-$ and the like. A particularly preferred cationic substituent of B or B' is a radical —$C(O)OY_7$ wherein $Y_7$ is $C_2$–$C_4$-alkyl, which is substituted by —$N(C_1$–$C_2$-alkyl$)_3^+$ $An^-$ and is further substituted by hydroxy, and $An^-$ is an anion, for example the radical —C(O)O—$CH_2$—CH(OH)—$CH_2$—$N(CH_3)_3^+An^-$.

(iv) Zwitterionic Substituents —$R_5$—Zw:

$R_5$ is a preferably a carbonyl, ester or amide functional group and more preferably an ester group—C(O)—O—.

Suitable anionic groups of the moiety Zw are for example —$COO^-$, —$SO_3^-$, —$OSO_3^-$, —$OPO_3H^-$ or bivalent —O—$PO_2^-$— or —O—$PO_2^-$—O—, preferably a group —$COO^-$ or —$SO_3^-$ or a bivalent group —O—$PO_2^-$—, and in particular a group —$SO_3^-$.

Suitable cationic groups of the moiety Zw are for example a group —$NR_9R_9'R_9''{}^+$ or a bivalent group —$NR_9R_9'{}^+$—, wherein $R_9$, $R_9'$ and $R_9''$ are as defined above, and are each independently of the other, preferably hydrogen or $C_1$–$C_6$-alkyl, preferably hydrogen or $C_1$–$C_4$-alkyl and most preferably each methyl or ethyl.

The moiety Zw is for example $C_2$–$C_{30}$-alkyl, preferably $C_2$–$C_{12}$-alkyl, and more preferably $C_3$–$C_8$-alkyl, which is in each case uninterrupted or interrupted by —O— and substituted or interrupted by one of the above-mentioned anionic and cationic groups each, and, in addition, is further unsubstituted or substituted by a radical —$OY_8$, wherein $Y_8$ is hydrogen or the acyl radical of a carboxylic acid.

$Y_8$ is preferably hydrogen or the acyl radical of a higher fatty acid.

Zw is preferably $C_2$–$C_{12}$-alkyl and even more preferably $C_3$–$C_8$-alkyl which is substituted or interrupted by one of the above-mentioned anionic and cationic groups each, and in addition may be further substituted by a radical —$OY_8$.

A preferred group of zwitter-ionic substituents —$R_5$—Z corresponds to the formula

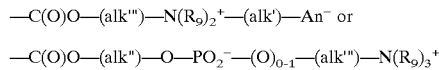

wherein $R_9$ is hydrogen or $C_1$–$C_6$-alkyl; $An^-$ is an anionic group —$COO^-$, —$SO_3^-$, —$OSO_3^-$ or —$OPO_3H^-$, preferably —$COO^-$ or —$SO_3^-$ and most preferably —$SO_3^-$, alk' is $C_1$–$C_{12}$-alkylene, (alk'') is $C_2$–$C_{24}$-alkylene which is unsubstituted or substituted by a radical —$OY_8$, $Y_8$ is hydrogen or the acyl radical of a carboxylic acid, and (alk''') is $C_2$–$C_8$-alkylene.

(alk') is preferably $C_2$–$C_5$-alkylene, more preferably $C_2$–$C_6$-alkylene and most preferably $C_2$–$C_4$-alkylene. (alk'') is preferably $C_2$–$C_{12}$-alkylene, more preferably $C_2$–$C_6$-alkylene and particularly preferably $C_2$–$C_3$-alkylene which is in each case unsubstituted or substituted by hydroxy or by a radical —$OY_8$. (alk''') is preferably $C_2$–$C_4$-alkylene and more preferably $C_2$–$C_3$-alkylene. $R_9$ is hydrogen or $C_1$–$C_4$-alkyl, more preferably methyl or ethyl and particularly preferably methyl. A preferred zwitterionic substituent of B or B' is of formula

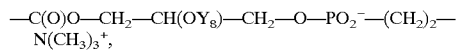

wherein $Y_8$ is hydrogen or the acyl radical of a higher fatty acid.

In one embodiment of the invention one of B and B' may also be the radical of a hydrophobic comonomer which includes especially those customarily used in the manufacture of contact lenses. Suitable hydrophobic vinylic comonomers include, without the list being exhaustive acrylonitrile, methacrylonitrile, vinyl-$C_1$–$C_{18}$-alkanoates, $C_2$–$C_{18}$-alkenes, $C_2$–$C_{18}$-haloalkenes, styrene, $C_1$–$C_6$-alkylstyrene, $C_2$–$C_{10}$-perfluoroalkyl acrylates and methacrylates or correspondingly partially fluorinated acrylates and methacrylates, $C_3$–$C_{12}$-perfluoroalkyl-ethyl-thiocarbonylaminoethyl acrylates and methacrylates, acryloxy- and methacryloxy-alkylsiloxanes, N-vinylcarbazole and the like. Examples of suitable hydrophobic vinylic comonomers include acrylonitrile, methacrylonitrile, vinyl acetate, vinyl propionate, vinylbutyrate, vinyl valerate, styrene, chloroprene, vinyl chloride, vinylidene chloride, 1-butene, butadiene, vinyltoluene, perfluorohexylethylthiocarbonylaminoethyl methacrylate, trifluoroethyl methacrylate, hexa-fluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl)tetramethyldisiloxane.

B denotes for example a radical of formula

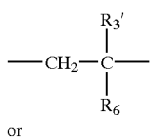
(11a)

or

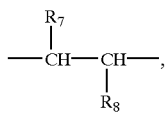
(11b)

wherein $R_3'$ is hydrogen or $C_1$–$C_4$-alkyl, preferably hydrogen or methyl; $R_6$ is a hydrophilic substituent, wherein the above given meanings and preferences apply; $R_7$ is $C_1$–$C_4$-alkyl, phenyl or a radical —C(O)OY$_9$, wherein Y$_9$ is hydrogen or unsubstituted or hydroxy-substituted $C_1$–$C_4$-alkyl; and $R_8$ is a radical —C(O)Y$_9'$ or —CH$_2$—C(O)OY$_9'$ wherein Y$_9'$ independently has the meaning of Y$_9$.

$R_7$ is preferably $C_1$–$C_2$-alkyl, phenyl or a group —C(O)OY$_9$. $R_8$ is preferably a group —C(O)OY$_9'$ or —CH$_2$—C(O)OY$_9'$ wherein Y$_9$ and Y$_9'$ are each independently of the other hydrogen, $C_1$–$C_2$-alkyl or hydroxy-$C_1$–$C_2$-alkyl. Particularly preferred —CHR$_7$–CHR$_8$— units according to the invention are those wherein $R_7$ is methyl or a group —C(O)OY$_9$ and $R_1$ is a group —C(O)OY$_9'$ or —CH$_2$—C(O)OY$_9'$ wherein Y$_9$ and Y$_9'$ are each hydrogen, $C_1$–$C_2$-alkyl or hydroxy-$C_1$–$C_2$-alkyl.

B' independently may have one of the meanings given above for B or is the radical of a hydrophobic comonomer, for example the radical of one of the above-given hydrophobic comonomers.

If (oligomer) is a telomer radical of formula (10), the radical —(alk)—S—[B]$_p$—[B']$_q$—Q preferably denotes a radical of formula

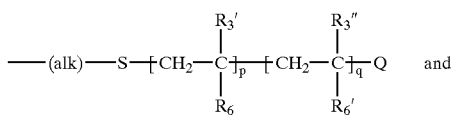 and
(10')

even more preferably of the formula

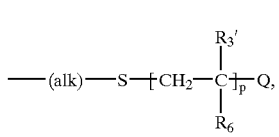
(10'')

wherein for $R_3'$, $R_6$, Q, p and q the above-given meanings and preferences apply, for $R_3''$ independently the meanings and preferences given before for $R_3'$ apply, and for $R_6'$ independently the meanings and preferences given before for $R_6$ apply or $R_6'$ is a hydrophobic substituent selected from the group consisting of hydrogen, —CN, $C_1$–$C_{18}$-alkanoyl, $C_1$–$C_{16}$-alkyl, $C_1$–$C_{16}$-haloalkyl, phenyl, $C_1$–$C_6$-alkylphenyl, $C_2$–$C_{10}$-perfluoroalkyloxycarbonyl or a corresponding partially fluorinated alkyloxycarbonyl radical, $C_3$–$C_{12}$-perfluoroalkyl-ethyl-thio-carbonylaminoethyloxycarbonyl, alkylsiloxyloxycarbonyl and carbazolyl.

A preferred group of suitable hydrophilic macromers according comprises compounds of the above formula (9) wherein $R_4^*$ is hydrogen or methyl, $R_4$ is hydrogen, methyl or carboxyl, $R_4'$ is hydrogen, $A_3$ is a radical of the above formula (6a), (6b) or (6e), wherein n and m are each 0 or 1, $X_1$ $X_3$ and $X_4$ are each independently of the other —O— or —NH—, A1 is unsubstituted or hydroxy-substituted —O—$C_2$–$C_8$-alkylene or a radical —O—$C_2$–$C_6$-alkylene—NH—C(O)—, $A_2$ is $C_1$–$C_4$-alkylene, phenylene or benzylene, (alk*) is $C_2$–$C_4$-alkylene, and (oligomer) denotes a radical of formula

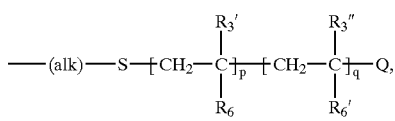
(10')

wherein (alk) is $C_2$–$C_6$-alkylene, Q is a monovalent group that is suitable to act as a polymerization chain-reaction terminator, p and q are each an integer of from 0 to 100 and the total of (p+q) is from 5 to 100, $R_3'$ and $R_3''$ are each independently of the other hydrogen or methyl, and for $R_6$ and $R_6'$ each independently of the other the meanings and preferences given before apply.

A more preferred group of suitable hydrophilic macromonomers according to the invention comprises compounds of formula

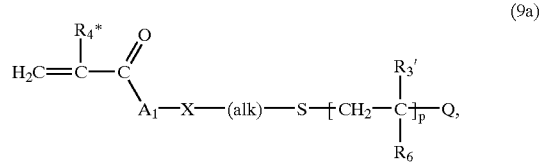
(9a)

wherein $R_4^*$ is hydrogen or methyl, $A_1$ is —O—(CH$_2$)$_{2-4}$—, —O—CH$_2$—CH(OH)—CH$_2$— or a radical —O—(CH$_2$)$_{2-4}$—NH—C(O)—, X is —O— or —NH—, (alk) is $C_2$–$C_4$-alkylene, Q is a monovalent group that is suitable to act as a polymerization chain-reaction terminator, p is an integer from 5 to 50, $R_3'$ is hydrogen or methyl, and for R6 the above given meanings and preferences apply.

Particularly preferred macromonomers comprise those of formula

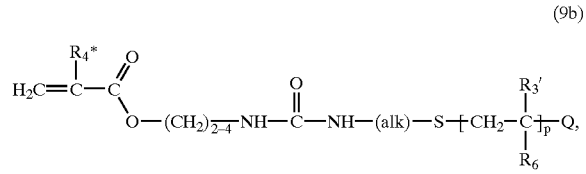
(9b)

wherein for $R_4^*$, $R_3'$, $R_6$, Q, (alk) and p the above-given meanings and preferences apply. A particularly preferred group of hydrophilic macromonomers are compounds of the above formula (9b) wherein $R_4^*$ is hydrogen or methyl, (alk) is $C_2$–$C_4$-alkylene, $R_3^1$ is hydrogen or methyl, p is an integer of 5 to 50, Q is as defined before, and for $R_6$ the above given meanings and preferences apply. Particularly preferably, the radical —CH$_2$—C(R$_3'$)(R$_6$)— in brackets in formula (9b) is the 1,2-ethylene radical derived from acrylamide, N,N-dimethyl acrylamide or N-vinylpyrrolidone.

The weight average molecular weight of the macromonomers that are optionally employed in the invention depends principally on the desired properties and is for example from 300 to 12000, preferably from 300 to 8000, more preferably from 300 to 5000, and particularly preferably from 500 to 2000.

The macromonomers of formula (9) may be prepared by methods known per se. For example, the compounds of formula (9) wherein A is a radical of formula (6a), (6b) or (6c) are obtainable by reacting a compound of formula

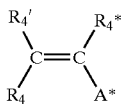 (7a)

wherein $R_4$, $R_4'$ and $R_4^*$ each have the above-given meaning and $A^*$ is, for example, a group —C(O)—$A^{}$, wherein $A^{}$ is halogen, particularly chlorine, an ester group an oxyalkylene radical comprising an epoxy group, for example the radical

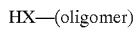

or is a radical —O—
$C_2$–$C_{12}$-alkylene-N═C═O; or $A^*$ is a radical —$(A_2)_m$—N═C═O or —$(A_4)_t$—N═C═O, wherein $A_2$, $A_4$, m and t each have the above-given meaning, with a compound of formula HX—(oligomer) (8a), wherein X and (oligomer) each have the above-given meaning.

The reactions of a compound of formula (7a) having a carboxylic acid halide group, an epoxy group or an isocyanato group with an amino or hydroxy compound of formula (8a) are well-known in the art and may be carried out, for example, as described above concerning the reaction of the compounds of formula (7) with the compounds of formula (8).

Moreover, the macromonomers of formula (1) wherein A is a radical of formula (6c) or (6e) may be obtained by reacting a compound of formula

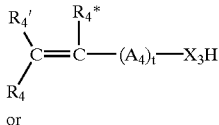 (7b)

or

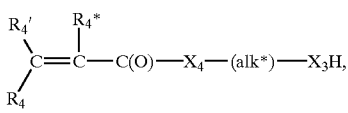 (7c)

wherein $R_4$, $R_4'$, $R_4^*$, $A_4$, $X_3$, $X_4$, (alk*) and t each have the above-given meaning, with a compound of formula —$X_1'$(O)C—(oligomer) (12), wherein (oligomer) has the above-given meaning and $X_1'$ is for example —OH or halogen, in particular chlorine, or together with —(O)C— forms an anhydride group, in a manner known per se.

The macromonomers of the formula

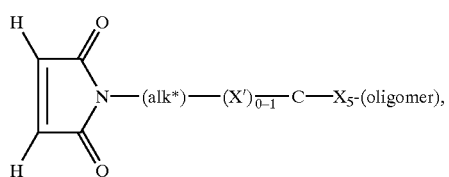 (9c)

wherein (alk*), X', $X_5$ and (oligomer) each have the above-given meaning, may be obtained in a manner known per se, for example, by reacting a compound of formula

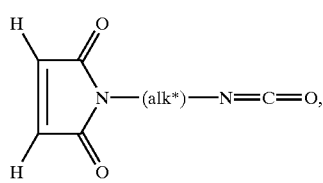 (7d)

wherein (alk*) has the above-given meaning, with a compound of the above-given formula (6), or by reacting a compound of formula

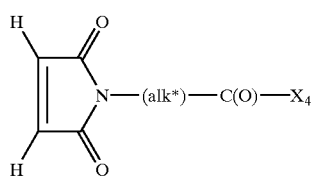 (7e)

with a compound of the above formula (8a) wherein (alk*) and $X_4$ each have the above-given meaning.

The compounds of the formula (7a), (8a), (7b), (7c), (7d) and (7e) are known compounds which are commercially available or may be prepared according to known methods. For example, compounds of the formula (7a) and (8a) wherein (oligomer) denotes a radical of formula (6a) and their manufacture are known for example from PCT application WO 92/09639.

The co-grafts-polymerization of one or more acceptor saccharides comprising a C—C double bond and one or more hydrophilic macromonomers, for example of the above formula (9), may be performed by processes known per se, for example by photopolymerizing a mixture of the acceptor saccharide(s) and the macromonomer(s) according to a process as outlined above.

By means of the above-described coating process, the acceptor saccharides, optionally in admixture with a hydrophilic macromonomer, may be grafted to the bulk material surface with formation of a coating having for example a so-called bottle brush-type structure (BBT) composed of tethered "hairy" chains. Such BBT structures in one embodiment comprise a long hydrophilic or hydrophobic backbone which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains.

The enzymatical attachment of the further carbohydrate (s) to the acceptor saccharide may take place before or after the covalent bonding of the acceptor saccharide to the surface of the ophthalmic molding. According to one embodiment of the invention, the further carbohydrate(s) are previously enzymatically attached to the acceptor saccharide, for example in solution, and the carbohydrate thus obtained is then, optionally after a work-up or a purification step, covalently bonded to the surface of the ophthalmic molding, for example according to one of the methods as outlined above. According to a further embodiment of the invention, the acceptor saccharide is first of all bonded covalently to the surface of the ophthalmic molding, and to the acceptor saccharides thus immobilized is then enzymatically attached the further carbohydrate(s).

The attachment of a further carbohydrate to an acceptor saccharide immobilized on the substrate surface or in solution occurs advantageously by reacting the carbohydrate with the acceptor saccharide units in the presence of an enzyme, in particular in the presence of a glycosyltransferase. The attachment of the further carbohydrate thus comprises the transfer of a glycosyl group from a donor to an acceptor by means of a specific glycosyl transferase. The donor is suitably an enzyme substrate which is activated with the glycosyl group to be transferred, e.g. a nucleoside. The acceptor saccharides being present on the modified surface of the opthalmic molding or in solution function as acceptor molecules. Glycosyltransferases suitable to aid selectively attaching a carbohydrate, for example the above-mentioned carbohydrates, to an acceptor saccharide are known to the art-skilled worker and can be taken from textbooks of enzyme chemistry, for example from D. Schomburg, D. Stephen (Eds.), Enzyme Handbook 12, Class 2.3.2-2.4, Transferases, Springer Berlin, Heidelberg, New York, Tokyo 1996. The textbook discloses i.a. suitable sialyl transferases, galactosyl transferases, fucosyl transferases, mannosyl transferases, glucosyl transferases or xylosyl transferases.

Suitable reaction media and conditions, for example appropriate enzyme substrates and other optional ingredients such as proteins, buffers and the like are known to the art-skilled worker or conveniently may be taken from the above-mentioned textbooks.

A further embodiment of the invention comprises further sulfating the primarily generated surface—comprising the covalently bonded acceptor saccharides and the enzymatically attached further carbohydrate—enzymatically by using, for example, adenosine-3'-phosphate-5'-phosphosulfate (PAPS) as donor moiety and a sulfo-transferase as enzyme.

The enzymatic attachment of carbohydrates according to the invention enables one to generate complex oligo- or polysaccharide structures on the surface of the ophthalmic molding by applying one or more different carbohydrates, in particular one or more different monosaccharides, in the presence of one or more different glycosyltransferases. In case of different carbohydrates to be attached, the enzymes may be applied sequentially one-by-one or as combinations of several enzymes, together with the corresponding enzyme substrate in each case. Depending on the nature of the terminal sugar radicals present on the modified surface obtained, the enzymes elongate and/or crosslink the carbohydrate structure on the material surface in accordance with the specifity of the enzymes and the substrates present in the reaction mixture.

The coating thickness of the carbohydrate coating comprising the acceptor saccharides and the enzymatically attached further carbohydrates on the surface of the ophthalmic molding depends principally on the desired properties. It can be, for example, from 0.001 to 1000 $\mu$m, preferably from 0.01 to 500 $\mu$m, more preferably from 0.01 to 100 $\mu$m, even more preferably from 0.05 to 50 $\mu$m, especially preferably from 0.1 to 5 $\mu$m and particularly preferably from 0.1 to 1 $\mu$m.

The carbohydrate modified surfaces of the ophthalmic moldings obtained according to the invention may be purified afterwards applying conventional techniques such as for example washing or extraction with a solvent like water, methanol, ethanol and the like. The characterization of the surfaces obtained may be performed by various techniques including X-ray Photoelectron Spectroscopy (XPS) or Time Of Flight Secondary Ion Mass Spectrometry (TOF-SIMS).

Suitable ophthalmic moldings according to the invention are, for example, contact lenses including both hard and particularly soft contact lenses or any kind of ocular prostheses such as corneal implants, in particular intraocular lenses or artificial cornea.

The ophthalmic devices according to the invention have a variety of unexpected advantages over those of the prior art which make those devices very suitable for practical purposes, e.g. as contact lens for extended wear or intraocular lens. For example, they do have a high surface wettability which can be demonstrated by their contact angles, their water retention and their water-film break up time or tear film break up time (TBUT).

The TBUT plays an particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Taking into account the average time period between two blinks of an eye it follows that a wettable and biocompatible contact lens should hold a continuous layer of tear fluid for more than 10 seconds and preferably for more than 15 seconds. Whereas current biomedical materials in general have TBUTs of well below 10 seconds and thus do not reach this target, the composite materials of the present invention have TBUTs of >10 seconds and especially >15 seconds. In addition, the TBUT of commercial contact lenses may be improved considerably by applying a surface coating according to the invention. On the base curve of a contact lens, the pronounced lubricity of the coating facilitates the on-eye lens movement which is essential for extended wear of contact lenses. Moreover, the moldings of the invention provide additional effects being essential for lenses for extended wear, such as an increased thickness of the pre-lens tear film which contributes substantially to low microbial adhesion and resistance to deposit formation. Due to the extremely soft and lubricious character of the novel surface coatings, the ophthalmic moldings of the invention such as in particular contact lenses show a superior wearing comfort including improvements with respect to late day dryness and long term (overnight) wear. The novel surface coatings moreover interact in a reversible manner with occular mucus which contributes to the improved wearing comfort.

In addition, ophthalmic devices obtainable according to the present invention have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the ophthalmic moldings of the invention is excellent. In addition, the carbohydrate modified surface on a given bulk material according to the invention does not affect its visual transparency.

In addition, the moldings of the present invention having a carbohydrate modified surface are capable of interacting with human or animal tissue cells and support the attachment and growth of human or animal cells in vivo or in vitro, which make those devices very suitable for practical purposes, e.g. as corneal implant, in particular as intraocular lens or artificial cornea.

Corneal implants may be placed by way of conventional surgery techniques beneath, within, or through corneal epithelial tissue, or within the corneal stroma or other tissue layers of the cornea. Such implants may change the optical properties of the cornea (such as to correct visual deficiencies) and/or change the appearance of the eye, such as pupil coloration. A corneal implant may comprise an optical axis region which on implantation covers the pupil and provides visual acuity, and a less transparent region which surrounds the periphery of the optical axis region. Alternatively the implant may have the same visual acuity across its dimensions.

In summary, the ophthalmic devices according to the invention, such as contact lenses and artificial cornea, provide a combination of (i) low spoilation with respect to cell debris, cosmetics, dust or dirt, solvent vapors or chemicals, (ii) a high comfort for the patient wearing such opthalmic devices in view of the soft hydrogel surface which for example provides a very good on-eye movement of the ohtalmic device and (iii) biocompatibility, bioadhesion, cell accumulation, molecular recognition and cell attachment.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wvilhelmy method using a Krüss K-12 instrument (Krüss GmbH, Hamburg, Germany). Wetting force on the solid is measured as the solid is immersed in or withdrawn from a liquid of known surface tension.

PLASMA TREATMENT

EXAMPLE A-1

1,2-Diaminocyclohexane Coating (DACH)

Two dried Lotrafilcon A contact lenses (CIBA Vision Corp., Atlanta, USA) are, after extraction in isopropanol, toluene and again in isopropanol, placed on the glass holder within the plasma reactor equipped with an external ring electrode and a 27.13 MHz radiofrequency (RF) generator for the generation of an capatively-coupled, cold glow discharge plasma. The distance between the substrates and the lower edge of the plasma zone is 12 cm. The reactor is evacuated to a pressure of 0.008 mbar, and held at these conditions for one hour. Then, the argon plasma gas flow rate into the plasma zone of the reactor is set to 20 sccm (standard cubic centimeter), the pressure in the reactor is adjusted to 0.12 mbar and the RF generator is switched on. The plasma discharge of a power 250 Watts is maintained for a total period of 1 min (in order to clean and activate the lenses surfaces). Afterward the 1,2-DACH vapor is introduced into the reactor chamber from DACH reservoir (maintained at 24° C.) at 0.15 mbar for 1 min. After this, the following parameters for the plasma polymerization of DACH are chosen Argon flow rate for plasma excitation=5 sccm, Argon carrier gas flow rate for DACH transport=5 sccm, temperature of the DACH evaporation unit=24 ° C., the distance between the lower edge of the plasma zone and the substrates=5 cm, pressure=0.2 mbar, and plasma power= 100 W. The lenses are treated for about 5 minutes with a pulsing glow discharge plasma (1 μsec. on, 3 μsec. off). After 5 minutes of deposition the plasma discharge is interrupted and DACH vapor is let to flow into reactor for other 5 min. The reactor is then evacuated and maintained for 30 minutes at a pressure 0.008 mbar in order to remove residual monomer and activated spices. The internal pressure is brought to atmospheric by using dry nitrogen. The substrates are then turned over and the whole procedure is repeated to coat the other side of the substrates.

The samples are then unloaded from the reactor and used for subsequent reactions.

EXAMPLE A-2

Plasma Induced 2-Isocyanatoethyl Methacrylate Coating (Poly-IEM1)

The substrates including two PVP free polycarbonate membrane filters of a diameter 8 mm (Poretics Corporation, Livermore, USA), 2 Lotrafilcon A contact lenses and 2 Alsacon NC contact lenses (prepared as described in U.S. Pat. No. 5,760,100, 1998, CIBA Vision Corp.) are, after extraction in isopropanol, placed on the teflon holder within the plasma reactor equipped with an external ring electrodes. The distance between the substrates and the lower edge of the plasma zone is 12 cm. The reactor is evacuated to a pressure of 0.010 mbar, and held at these conditions for one hour. Then, the argon plasma gas flow rate into the plasma zone of the reactor is set to 20 sccm, the pressure in the reactor is adjusted to 0.07 mbar and the RF generator (27.12 MHz radio frequency generator, HFA Koppold & Co., Höhenkirchen, Germany) is switched on. The plasma discharge of a power 170 Watts is maintained for a total period of 1 min. Afterward the IEM vapor is introduced into the reactor chamber from IEM reservoir (maintained at 25° C.) at 0.15 mbar for 1 min. After this, the following paramerers for the plasma induced polymerization of IEM are chosen Argon flow rate for plasma excitation=20 sccm, Argon carrier gas flow rate for monomer (IEM) transport=10 sccm, temperature of the monomer (IEM) evaporation unit=25° C., the distance between the lower edge of the plasma zone and the substrates=16 cm, pressure=0.10 mbar, and plasma power=160 W. After 5 minutes of deposition the plasma discharge is interrupted, the reactor is evacuated and maintained for 30 minutes at a pressure 0.010 mbar. The internal pressure is then brought to atmospheric by using dry nitrogen. The substrates are then turned over and the whole procedure is repeated to coat the other side of the substrates.

The samples are then unloaded from the reactor and analyzed by Fourier Transform Infrared-Attenuated Total Reflection Mode measurements (FTIR-ATR). Strong bands at about 2270 cm-1, which are characteristic for N=C=O groups, are clearly identified on all modified surfaces.

EXAMPLE A-3

Plasma Induced 2-Isocyanatoethyl Methacrylate Coating (Poly-IEM2)

The substrates used for this coating are 8 pieces of PVP free polycarbonate membranes (Poretics Corporation, Livermore, USA) of a diameter 4 mm and 10 pieces of Z-Por lenticules of a diameter 4 mm (prepared according to EP-A-0889923). The substrates are positioned in the reactor at the distance 15 cm from the lower edge of the plasma zone. The reactor is then evacuated to a pressure 0.012 mbar and maintained at this pressure for 40 min. The argon plasma gas flow rate into the plasma zone is set to 20 sccm, the pressure in the reactor is adjusted to 0.10 mbar and the RF generator is switched on. The plasma discharge of the power of 200 W is maintained for a total period of 1 minute, and then, the reactor is once again evacuated to a pressure 0.012 mbar. After repositioning of the substrates on the distance of 20 cm from the bottom of the plasma zone, the argon flow rate into the plasma zone is set to 20 sccm, the argon flow rate through the IEM reservoir, maintained at 25° C., is set to 10 sccm, the pressure in the reactor is adjusted to 0.20 mbar and the plasma discharge is initiated. IEM is polymerized for 5 minutes at 180 Wafts plasma power. At the end of the reaction period, the monomer vapor is still introduced in the postdischarge region for 15 minutes. Then the base pressure of 0.012 mbar is restored and maintained for 30 min. The reactor pressure is then raised to atmospheric with nitrogen. After coating the other sides with the same procedure, the substrates are analyzed by ATR-FTIR spectroscopy. Strong bands at about 2270 cm-1, which are characteristic for N=C=O groups, are clearly identified on all modified surfaces.

PREPARATION OF AN ACCEPTOR SACCHARIDE AND ENXYMATIC ATTACHMENT OF A FURTHER CARCONHYDRATE

EXAMPLE B-1

Preparation of N-(8-Aminooctyl) Lactobionic Acid Amide as an Aminoalkyl Functionalized Galactose Derivative A suspension of 40 g (0.12 Mol) of Lactobionolactone (Solvay, Germany) in 400 ml of Methanol is added to a solution of 22 g (0.15 Mol) of 1,8-diaminooctane in 200 ml of Methanol stirring in a three-neck flask equipped with thermometer, a mechanical stirrer and a reflux condenser. After 24 hours of reflux under a nitrogen atmosphere, 5 g of activated charcoal is added to the flask and after 5 minutes of stirring the solution is filtered through a 1 cm thick layer of Silicagel and Hyflo. A slightly yellow solution is then concentrated on Rotavapor to a volume about 100 ml and after cooling to ~5° C. 20 ml of acetonitrile and 20 ml of diethyl ether are added to initiate a crystallization. After 3 days of standing at 5° C., the crystalline product which is believed to conform to the formula

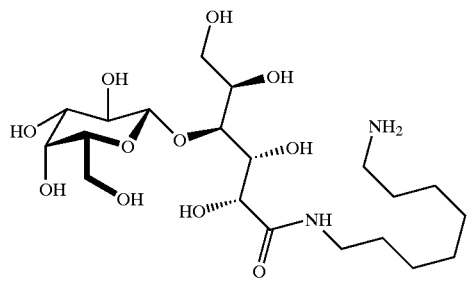

is filtered off and dried under a reduced pressure for 12 hours.

Elemental analysis: %C %H %N; Calcul. 49.588.32 5.78; Found 48.687.99 5.56.

Titration of amino groups: 2.06 mVal/g (titration with 0.1 N $HClO_4$).

BEISPIEL B-2

Preparation of Other N-(Aminoalkyl)lactobionic Acid Amides

Analogously to the example B-1, Lactobionolactone is reacted with 1,2-diaminoethane, 1,6-diaminohexane or 1,10-diaminodecane in order to prepare the corresponding molecules which contain spacer moieties of 2, 6, and 10 carbon atoms.

BEISPIEL B-3

Preparation of N-Benzyloxycarbonyl, N'-(8-Aminooctyl)lactobionic Acid Amide

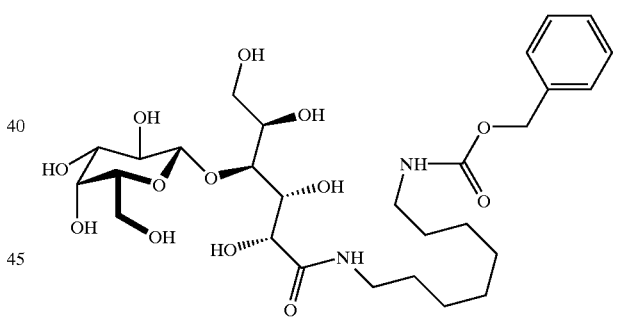

A solution containing 40g (0.12 moles) lactobionolactone in 400 mL methanol (dry) is slowly added to a clear solution of 22,1 g (0.15 mols) 1,8-diaminooctane in 200 mL methanol (dry). This reaction is performed in a three-neck flask equipped with thermometer, mechanical stirrer and reflux condenser. The obtained reaction solution is heated overnight at 75° C. under a nitrogen atmosphere. A brown solution is formed which is subsequently mixed with 5 g activated charcoal and filtered hot through a G4 glass filter funnel (Duran) using Hyflo as a filter aid. The yellow filtrate is then concentrated on a Rotavapor to a final volume of approximately 100 mL. 40 mL acetonitrile and 20 mL diethyl ether are added. After overnight cooling in a refrigerator (5° C.) 28,5 g (50% ) a yellow solid had precipitated from the solution.

The yellowish raw product is dissolved in 500 mL methanol. At room temperature 20 mL triethylamine (0.14 moles) and 16,5 mL (0.12 moles) benzyl-chloroformate (d:1,21) are added dropwise. The reaction mixture is stirred for 4 hours at 25° C. and then filtered through Hyflo on a G4 glass filter funnel. After evaporation of the solvent 57 g of a brown solid are obtained. The raw product is purified by column chromatography using Silicagel 60 (Fluka) and a mixture of methylene chloride/methanol/water 10/2/0.2 as the eluent. 8.3 g of a white solid (yield 22.6%) are obtained.

Thin layer chromatography (using the same eluent as above and silica TLC plates; $R_f$ value of the benzyloxy derivative 0.8; for comparison $R_f$ value of the intermediate amino derivative: 0.1) confirmed the high purity of the product.

EXAMPLE B-4

Enzymatic Sialidation of N-(1-n-Octyl)lactobionic Acid Amide

To a reaction mixture containing 45 mL Hepes buffer, 100 mM, pH=7.0; 2.5 mL 2,3 Dehydro-2-desoxy-N-acetyl-neuraminic acid, 0.1M; 4.5 mL bovine serum albumine (BSA), 10 mg/mL; 3 mL CMP-Neu5Ac, 6 mM and 1 mL CMP-Neu5Ac[C14] 0.5 mL of N-(1-amino-n-octyl) lactobionic acid, 37 mM and 0.2 mL soluble rat a(2–3) Sialyltransferase, 25 U/mL are added. After incubation for 10 minutes at 37° C. the reaction is stopped by the addition of 1 mL $H_2O$. The total volume is loaded onto a 1 ml Sep-Pak Plus C18 cartridge (Waters, WAT020515), washed with 5 mL $H_2O$ and eluted with 6 mL methanol. All fractions are counted for C14 in a scintillation counter. The ratio between the counts in the methanol fraction, containing the sialidated product, and the total counts are used as a measure for product formation.

[C14] CMP-Neu5Ac: Amersham CFB165 B73, 261 mCi/mmol, 50 mCi/2 mL

Hepes=4-(2-Hydroxyethyl)-piperazine-1-ethane-sulfonic acid (FLUKA,54461)

EXAMPLE B-5

Enzymatic Sialidation of N-Benzyloxycarbonyl, N'-(8-Amino-octyl)lactobionic Acid Amide In a 250 ml plastic bottle with a magnetic stir bar 506.3 mg (0,82 mmoles) of the product prepared in example B-3, are dissolved in 26 mL water and 16 mL DMSO. After 30 min a clear solution is formed. Then 698 mg CMPsia (1.06 mmoles), 49.1 mg BSA, 64 mL NaCaCo 0.05M pH6.5 and 64 mL 0,06 M aqueous $MnCl_2$ are added. After 10 min 20 μl of 2,3 Dehydro-2-desoxy-N-acetyl-neuraminacid 0.1M and 10 μl CIAP and 1 mIL $Sia_E$ (12 U/mL) are added and the solution is stirred for 2 days. The progress of the reaction is controlled by thin layer chromatography (see below). The product which is believed to conform to the formula

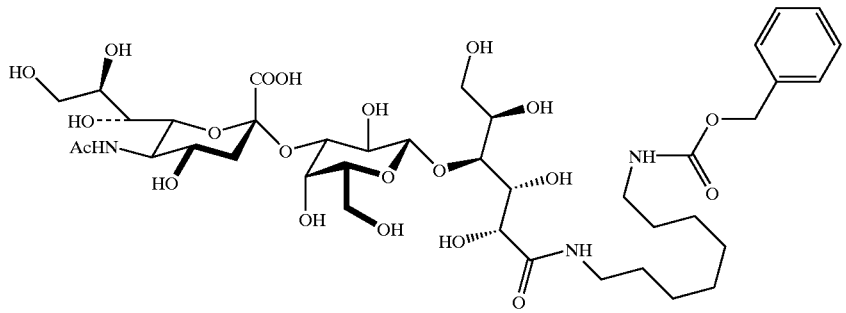

is isolated by adsorption on a reversed phase C-18 silica column from water and subsequent by desorption with methanol. The methanol fraction is evaporated on a Rotavapor, and a yellow oil is obtained.

Purification: Chromatography on a silica gel 60 column; elution: methylene chloride/methanol/water 101410.2. The pure sialidated product is isolated by desorption from the silica using ~700 ml methanol. 478.4 mg of a white solid (yield 64.2%) are obtained.

Thin layer chromatography (Eluent: methylene chloride/methanol/water 10/4/0.4): $R_f$ value of starting material from example B-3:0.64, $R_f$ value of sialidated product 0.32. $R_f$ value of sialidated product 0.32

Abbrevations: BSA=Bovine serum albumine (Boehringer); CIAP=Phospatase, grade I (Boeringer 108146); NaCaCo=Cacodylic acid sodium salt trihydrate; $MnCl_2$=Mangan (II) chlorid tetrahydrate; CMPsia=Sialic acid cytidine monophosphate (activated sialic acid, CMP-NANA); $Sia_E$=α(2-3)Sialyl-Transferase Enzyme.

EXAMPLE B-6

Enzymatic Sialidation of Other N-(Aminoalkyl) lactobionic Acid Amides

Analogously to the example B-5, the three lactobionic acid amides prepared as described in the example B-2 are enzymaticly sialidated. For the determination of relative rates of the enzymatic reaction the consumption of CNP-NANA as well as formation of CNP was recorded by using HPLC analysis of the reaction mixture.

HPLC system used comprised from 25 cm Nucleosil—NH2 column (Supelco Z22,612-2), 2 cm length pre-column (Supelco Z22,718-8) and UV detector. A mixture of 85% buffer A (50% 15 mM phosphate, pH=7.0 and 50% Acetonitrile) and 15% of buffer B (250 mM phosphate, pH=7.0) was used as eluent.

The relative rates found were as follows:

| Spacer $C_n$ | Rel. rate |
|---|---|
| 2 | 20 |
| 6 | 80 |
| 10 | 100 |

EXAMPLE B-7

Preparation of Sialidated N-(8-Aminooctyl)-N' (Lactobionic Acid Amide)

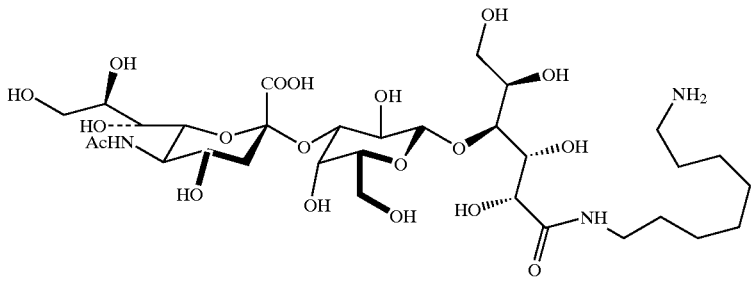

In a three-necked flask equipped with argon and hydrogen 400 mg (0.44 mmoles) of the product from example B-5 are dissolved under an argon blanket in a mixture of 8 mL water and 6 mL dioxane. A slightly yellowish solution is formed which is vigorously agitated in order to remove dissolved oxygen. After 15min under argon 193 mg of Palladium/activated charcoal (10% Pd) is added. The black suspension is then treated with hydrogen (1 bubble/sec) and the progress of the hydrogenation controlled by thin layer chromatography. After 3 hours the hydrogenation is completed and the pure product is isolated.

Isolation: The black reaction mixture is filtered trough a PTFE 0.2 um Filermembrane, the filtrate is frozen and lyophilised. The product is a white solid: 370 mg (yield 99%) Thin layer chromatography (Silica gel 60; F 254, detection: ninhydrine; elution solvent methylene chloride/methanol/water 6/4/1): $R_f$ value of product: 0.1

EXAMPLE B-8

Preparation of IEM-functionalized N-(8-Aminooctyl)lactobionic Acid Amide Solution 1.6 g of N-(8-Aminooctyl)lactobionic acid amide (amine titration=2.06 mEq/g), prepared by Example B-1 are dissolved in 18 ml of HPLC water. 5 ml of ethanol are added to the solution under stirring. Argon is then let to bubble through the solution for the period of about 30 minutes. 0.50 g of isocyanatoethyl methacrylate (IEM, isocyanate titration=6.45 mEq/g) are then slowly added to the solution under stirring. The whole mixture is then stirred under argon flow for 8 hours. No isocyanate groups are detected in the solution by FTIR measurements. The mixture is then filtered through 0.20 μm Teflon filter, degassed with pure nitrogen for 30 minutes in order to remove oxygen and used for photografting.

EXAMPLE B-9

Preparation of IEM-functionalized Sialidated N'-(8-Aminooctyl)lactobionic Acid Amide Solution

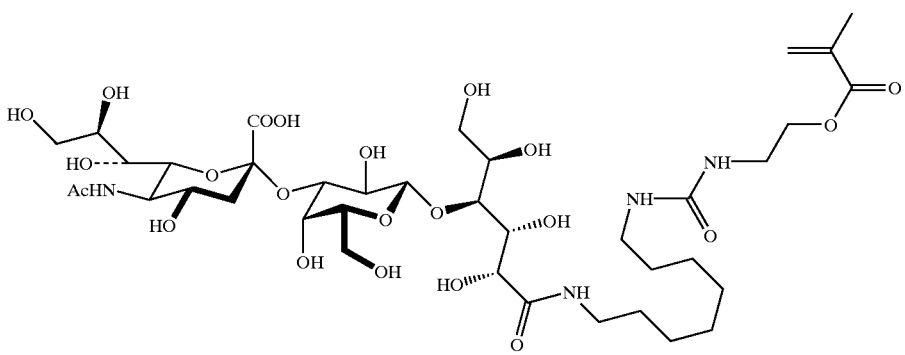

200 mg of sialidated N'-(8-aminooctyl)lactobionic acid amide (amine titration=1.29 mEq/g), prepared by Example B-7 are dissolved in 10 ml of buffer solution of pH=8.0 Argon is then let to 42bubble through the solution for the period of about 30 minutes. 0.04 g of isocyanatoethyl methacrylate (IEM, isocyanate titration=6.45 mEq/g) are then slowly added to the solution under stirring. The whole mixture is then stirred under argon flow for 6 hours. No isocyanate groups are detected in the solution by FTIR measurements. The macromonomer solution is then filtered through 0.20 μm Teflon filter, degassed with pure nitrogen for 30 minutes in order to remove oxygen and used for photografting.

EXAMPLE B-10

Preparation of Acrylamide Telomer

A 1000 mL three-necked round bottom flask is charged with a solution of 17.5 g (154 mmol) cysteamine hydrochloride (Fluka # 30080) in 150 deionized water. 1.1 g (4 mmol) α,α'-azodiisobutyramidine dihydrochloride (Fluka 11633) and a solution of 142 g (2 mol) acrylamide (Fluka 01696) in 450 mL deionized water are added. The pH of the solution is adjusted to pH=3 by addition of 1 molar hydrochloric acid. An intensive cooler and an internal thermometer are connected to the flask. The apparatus is evacuated to 100 mbar and filled with argon. This was repeated five times. The mixture was heated to 60° C. for three hours and then cooled to room temperature. An analytical sample is freeze-dried and the monomer conversion is determined by $^1$H-NMR spectroscopy. No resonances corresponding to C=C double bonds can be detected, indicating >98% conversion of the monomer.

The pH of the remaining mixture is adjusted to 10.5 by addition of 1 molar sodium hydroxide solution and diluted to a total volume of 1200 mL. Salts and low molecular weight residues such as unreacted chain transfer agent are removed by reverse osmosis using a Millipore Proscale system equipped with a Millipore Helicon RO-4 Nanomax 50 membrane operating at a pressure of 15 bar. The product is isolated from the obtained retentate by freeze-drying. Yield: 102 g of a white powder.

The concentration of amino groups is determined by functional group titration, result 0.22 mmol/g $NH_2$ corresponding to an average molecular weight of the telomer of 4500 g/mol. GPC-analysis indicates a monomodal molecular weight distribution and the absence of high molecular weight polymer.

EXAMPLE B-11

Preparation of IEM-functionalized Acrylamide Telomer Solution 12.4 g of acrylamide telomer with amino end group (amine titration=0.22 mEq/g), prepared by Example B-10 are dissolved in 85 ml of HPLC water. Argon is then let to bubble through the solution for the period of about 30 minutes. 0.45 g of isocyanatoethyl methacrylate (IEM, isocyanate titration=6.45 mEq/g) are then added to the solution under stirring. The whole mixture is then stirred under argon flow for 12 hours. No isocyanate groups are detected in the solution by FTIR measurements. The mixture is then filtered through 0.45 µm Teflon filter, degassed with pure nitrogen for 2×30 minutes in order to remove oxygen and used for photografting.

SURFACE BINDING

EXAMPLE C-1

Determination of Reactive Group Concentration on Modified Surfaces by the Reaction with Spin Label Molecules 4-Amino-2,2,6,6-tetramethyl-piperidin-1-oxyl (4-Amino-TEMPO)

8 isocyanate plasma modified substrates from Examples A-2 and A-3 are soaked in a solution of 0.05 g of 4-Amino-TEMPO (Fluka 09465) dissolved in a mixture of 1 ml of water and 4 ml of isopropanol. The isocyanate groups on the substrate surfaces reacted with spin label molecules at 25° C. for 4 hours. The substrates are then 3× ished in the same mixture (i-propanol/water 4:1) and extracted for 12 h in isopropanol. After having dried at reduced pressure of 0.010 mbar, the substrates are analyzed by ESR spectroscopy.

Concentration of spin label molecules on lens surfaces:

| Plasma coating from Example | Concentration (× $10^{-9}$ Mol spin/cm$^2$) |
| --- | --- |
| A-2 | 5.86 |
| A-3 | 9.89 |

EXAMPLE C-2

Coupling Reactions of Isocyanate Functionalized Poretics with N-(8-Aminooctyl)lactobionic Acid Amide (as an Aminoalkyl Functionalized Galactose Derivative)

15 Poretics membranes are surface modified with IEM according with the procedure described in Example A-3. Each membrane is separately immersed in 3 ml filtered (0.2 µm) 20% aqueous solution of isopropanol containing 30 mg of N-(8-aminooctyl)lactobionic acid amide synthetized by Example B-1. The surface reaction is proceed at 25° C. for 16 hours. Following the treatment, the membranes are extracted for 12 h in filtered 20% aqueous isopropanol to remove unreacted lactone-amid molecules. After this, the membranes are sent for epithelial cell attachment and growth tests.

EXAMPLE C-3

Coupling Reactions of Other Isocyanate Functionalized Substrates with N-(8-Aminooctyl) lactobionic Acid Amide (as an Aminoalkyl Functionalized Galactose Derivatives)

Analogously to Example C-2, 10 isocyanate functionalized Z-Por lenticules from Example A-3, 2 isocyanate functionalized Lotrafilcon A and 2 isocyanate functionalized Alsacon NC lenses from Example A-2 are coupled with N-(8-aminooctyl)lactobionic acid amide synthetized by Example B-1.

EXAMPLE C-4

Coupling Reactions of Amino Functionalized Substrates with Lactobionolactone

5 Poretics membranes are surface modified with 1,2-diaminocyclohexane (DACH) plasma according with the procedure described in Example A-1. Each membrane is then separately immersed in 3 ml solution of lactobionolactone (Solvay, Germany) in isopropanol/water mixture 1:4 (concentration 10 mg/ml), filtered through 0.2 µm teflon filter. The surface reaction is proceed at 40° C. for 16 hours. Following the treatment, the membranes are extracted for 12 h in filtered 20% aqueous isopropanol to remove unreacted lactone molecules. After this, the membranes are sent for epithelial cell attachment and growth tests.

EXAMPLE C-5

Enzymatic Sialidation of Poretics Membranes

7 Poretics membranes functionalized according to example C-2 are immersed in the following solution containing 880 mL Na-cacodylate, 0.5M, pH=6.5; 88 mL $MnCl_2$, 0.5M; 44 mL 2,3Dehydro-2-desoxy-N-acetyl-neuraminic acid, 0.1M; 26 mL BSA, 50 mg/mL; 16 mL CMP-Neu5Ac, 80 mM and 3.35 mL $H_2O$. Then 30 mL soluble rat α(2-3)Sialyltransferase, 14 U/mL and 9 mL CIAP, 15 U/mL are added and the reaction vessel placed on a rotary shaker for 4 hours at 37° C. Then the membranes are washed 3 times in 100 mL 0.5M NaCl, and stored at 4° C.

EXAMPLE C-6

Determination of Incorporation of Sialic Acid Molecules on N-(8-Aminooctyl)lactobionic Acid Amide Functionalized Poretics Membranes One functionalized Poretics membrane from example C-2 is incubated as described in Example C-5. In addition, the reaction mixture is spiked with [C14] radiolabelled CMP-Neu5Ac. The ratio between counts incorporated into the membrane and the total counts in the reaction mixture is used to calculate the total amount of Neu5Ac incorporated onto the membrane. Under the conditions used in Example C-4 an incorporation of 2.0 Neu5Ac/nm$^2$ is found.

EXAMPLE C-7

Enzymatic Sialidation of Z-Por Lenticules

The Z-Por lenticules, functionalized according to example C-3, are immersed in the following solution containing 7.5 mL Na-cacodylate, 0.5M, pH=6.0; 0.5 mL MnCl$_2$, 0.5M; 1 mL 2,3Dehydro-2-desoxy-N-acetyl-neuraminic acid, 0.1M; 1 mL BSA, 10 mg/mL; 2.5 mL CMP-Neu5Ac, 1.2mM, 5 mL CMP-Neu5Ac[C14] and 16.5 mL H$_2$O. Then 1 mL soluble rat α(2-3)Sialyltransferase, 14 U/mL and 0.2 mL CIAP, 15 U/mL are added and the reaction vessel is placed on a rotary shaker at 37° C. After incubation for 30 minutes the membranes are washed 4 times in 1 mL 0.5M NaCl, and the incorporated radioactivity measured in a scintillation counter. The surface loading of 1.8 sialic acid molecules/nm$^2$ was calculated from the counter.

EXAMPLE C-8

Enzymatic Sialidation of a Lotrafilcon a Contact Lens

A disc of 5 mm in diameter, prepared from the center of Lotrafilcon A contact lens functionalized according to Example C-3, is enzymatically sialidated. The disc is immersed in the following solution containing 7.5 mL Na-cacodylate, 0.5M, pH=6.5; 0.5 mL MnCl$_2$, 0.5M; 0.75 mL 2,3 Dehydro-2-desoxy-N-acetyl-neuraminic acid, 0.1M; 1 mL BSA, 10 mg/mL; 0.25 mL CMP-Neu5Ac, 6 mM; 5 mL CMP-Neu5Ac[C14] and 17 mL H$_2$O. Then 1 mL soluble rat α(2-3)Sialyltran 25 U/mL and 0.2 mL CIAP, 15 U/mL are added and the reaction vessel is placed on a rotary shaker for 38 minutes at 37° C. Then the membranes are washed 5 times in 1 mL 0.5M NaCl. The incorporated radioactivity is measured in a scintillation counter. The attachment of [C14] onto the lens piece is taken as a measure for the transfer of Neu5Ac.

EXAMPLE C-9

Enzymatic Sialidation of an Alsacon NC Contact Lens

A disc of 5 mm in diameter, prepared from the center of functionalized Alsacon lens (Example C-3), is enzymatically sialidated. The disc is immersed into the reaction mixture described for the modification of the Lotrafilcon A lens. After incubation for 38 minutes at 37° C. the membranes are washed 5 times with 1 mL 0.5M NaCl, and the incorporated radioactivity measured in a scintillation counter. The incorporation of [C14] into the lens is taken as a measure for the transfer of Neu5Ac.

EXAMPLE C-10

Surface Binding of the Reactive Photoinitiator Molecules

The aminofunctionalized contact lenses from Example A-1 are, immediately after plasma treatment with 1,2-DACH plasma, immersed into 1% acetonitrile solution of the reactive photoinitiator prepared by the addition reaction from isophorone diisocyanate and 4-(2-hydroxyethoxy) phenyl 2-hydroxy-2-propyl ketone (Darocure 2959) by the method described in EP-A-0632329. The amino groups on the lenses surfaces are reacted with the isocyanato groups of the photoinitiator molecules for 12 hours. After this time, the lenses are withdrawn from the reaction solution, washed and extracted in acetonitrile for 8 hours and dried under reduced pressure for 2 hours. The dried lenses are subsequently used for photografting.

EXAMPLE C-11

Surface Binding of the Reactive Photoinitiator Molecules

The aminofunctionalized contact lenses from Example A-1 are, immediately after plasma treatment with 1,2-DACH plasma, immersed into 1% acetonitrile solution of the reactive photoinitiator (II) prepared by the addition reaction from isophorone diisocyanate and 2-ethyl-2-(dimethylamino)-1-[4-(2-hydroxyethoxy)phenyl]-4-penten-1-one by the method described in WO 96/20796. The amino groups on the lenses surfaces are reacted with the isocyanato groups of the photoinitiator molecules for 16 hours. After this time, the lenses are withdrawn from the reaction solution, ished and extracted in acetonitrile for 12 hours and dried under reduced pressure for 2 hours. The dried lenses are subsequently used for photografting.

PHOTOGRAFTING

EXAMPLE D-1

Photografting of IEM-functionalized N-(8-Aminooctyl)lactobionic Acid Amide onto the Contact Lens Surface 1 ml of the degassed IEM-functionalized N-(8-Aminooctyl)lactobionic acid amide solution from Example B-8 is introduced into a small Petri dish of a volume of about 3 ml in a glow box. The dried lens from Example C-10, carrying covalently linked photoinitiator molecules on its surface, is then placed into this solution and an additional 1 ml of the degassed solution is added on the lens in order to cover the whole lens with the solution. After 15 minutes, the Petri dish with the lens in the solution is exposed to 15 mW ultraviolet light for a period of about 3 minutes. The lens is then turned over and the exposition is repeated by applying 15 mW UV light for an additional 3 minutes.

The modified lens is then withdrawn from the solution, ished twice in destined water, continuously extracted in ultra pure water for 16 h and analyzed by contact angle measurements.

Water/air contact angles on the modified lens are 15° adv., 0° rec., 15° hysteresis. In comparison, the contact angles of non-modified lens are 101° adv., 64° rec., 37° hysteresis.

EXAMPLE D-2

Photografting of IEM-functionalized Sialidated N'-(8-Aminooctyl)lactobionic Acid Amide onto the Contact Lens Surface 1 ml of the degassed IEM functionalized sialidated N'-(8-aminooctyl)lactobionic acid amide solution from Example B-9 is introduced into a small Petri dish of a volume of about 3 ml in a glow box. The dried lens from Example C-10, carrying covalently linked photoinitiator molecules on its surface, is then placed into this solution and an additional 1 ml of the degassed solution is added on the lens in order to cover the whole lens with the solution. After 10 minutes, the Petri dish with the lens in the solution is exposed to 15 mW ultraviolet light for a period of about 2 minutes. The lens is then turned over and the exposition is repeated by applying 15 mW UV light for an additional 2 minutes.

The modified lens is then withdrawn from the solution, ished twice in destined water, continuously extracted in ultra pure water for 6 h and analyzed by contact angle measurements. Water/air contact angles on the modified lens are 54° adv., 31° rec., 23° hysteresis. In comparison, the contact angles of non-modified lens are 101° adv., 64° rec., 37° hysteresis.

EXAMPLE D-3

Photografting of the Mixture of IEM-functionalized Sialidated N-(8-Aminooctyl)lactobionic Acid Amide Sialic Acid Derivative and IEM Functionalized Acrylamide Telomer onto the Contact Lens Surface 2 ml of the degassed solution from Example B-9 and 2 ml of the degassed solution from Example B-11 are mixed together and stirred for 5 minutes. 1 ml of the mixture is introduced into a small Petri dish of a volume of about 3 ml in a glow box. The dried lens from Example C-10, carrying covalently linked photoinitiator molecules on its surface, is then placed into this solution and an additional 1 ml of the degassed mixture is added on the lens in order to cover the whole lens with the solution. After 10 minutes, the Petri dish with the lens in the mixture is exposed to 15 mW ultraviolet light for a period of about 2 minutes. The lens is then turned over and the exposition is repeated by applying 15 mW UV light for an additional 2 minutes. The modified lens is then withdrawn from the solution, ished twice in destined water, continuously extracted in ultra pure water for 6 h and analyzed by FTIR ATR and contact angle measurements.

Water/air contact angles on the modified lens are 26° adv., 190 rec., 70 hysteresis. In comparison, the contact angles of non-modified lens are 101° adv., 64° rec., 37° hysteresis.
Clinical experiments

EXAMPLE E-1

In Vivo Testing of Corneal Epithelial Cell Attachment and Overgrowth on Surface-sialidated Poretics Membranes Used as a Model for an Artificial Cornea (Corneal Onlay Lenticule to be Re-overgrown by the Epithelium)

Cats used as animal models for in vivo testing are free of active ocular and systemic diseases. All animals have the nictitating membranes of both eyes surgically removed at least two weeks prior to the surgical implantation of the sialidated model membranes. The cats are then anaesthetisized by intramuscular injection. The corneal epithelium from a central 6 mm diameter area is removed by scraping with a scalpel. A trephine of 4 mm diameter is used to make a circular keratotomy. 150–200 $\mu$m in depth, in the central cornea. A 4 mm circular disc of a sialidated Poretics polycarbonate membrane (8 $\mu$m thick, 0,1 $\mu$m pore size, porosity 2,4 %) prepared as outlined in example C-5 is tucked into the circular pocket. Thus, a 4 mm-diameter central area of the sialidated membrane is exposed. Topical steroids, antibiotics and Sofradex eye drops are applied repeatedly to the operated eye in order to support wound healing. Clinical evaluation of the overgrowth of the implanted membrane is carried out daily for 45 days. Results obtained on two cats demonstrate clearly the fast and full recovery of the corneal epithelium and the perfect longterm integration of the implanted membrane (see table):

TABLE

| | Cat 1 | Cat 2 |
|---|---|---|
| days until 25% overgrowth, 1 cell layer | 1.5 | 1.5 |
| days until 50% overgrowth, 1 cell layer | 2.0 | 2.0 |
| days until 75% overgrowth, 1 cell layer | 2.5 | 2.5 |
| days until 100% overgrowth, 1 cell layer | 3.5 | 5.0 |
| days until 100% overgrowth, 5 cell layers | 20.0 | 25.0 |
| % surface coverage by 4–5 cell layers after 45 days on top of a full base coverage with 3 cell layers | 100 | 60 |

Surface Characterization of Modified Surfaces by TOF-SIMS

Three 8 mm Z-Por lenticules (fluoropolymer-based porous artificial cornea implant) are surface modified with the following coatings:

IEM downstream plasma coating according to example A-2

Lactobionic acid amide (LBAA) coating according to example C-2

Sialidated LBAA coating according to example C-5

The 3 Z-Por samples represent the 3 individual steps of the reaction sequence used to load the surface of the implant with the final sialic acid terminated oligosaccharide. The molar masses of the molecular fragments observed resulting from surface exposed groups of the 3 coatings demonstrate clearly the presence of the lactobionic acid amide and the sialidated lactobionic acid amide.

What is claimed is:

1. An ophthalmic molding comprising
   (a) a bulk material carrying covalently linked photoinitiator molecules for radical polymerization on its surface; and
   (b) a surface coating obtained by co-graft polymerizing onto the bulk material surface:
      (i) one or more different acceptor saccharides comprising an ethylenically unsaturated double bond; and
      (ii) one or more hydrophilic macromonomers of formula

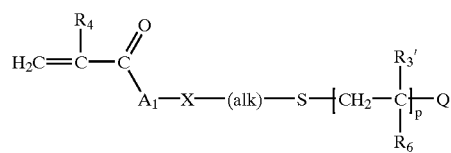

wherein $R_4^*$ is hydrogen or methyl, $A_1$ is —O—$(CH_2)_{2-4}$—, —O—$CH_2$—$CH(OH)$—$CH_2$— or a radical —O—$(CH_2)_{2-4}$—NH—C(O)—, X is —O— or —NH—, (alk) is $C_2$–$C_4$-alkylene, Q is a monovalent group that is suitable to act as a polymerization chain-reaction terminator, p is an integer from 5 to 50, $R_3'$ is hydrogen or methyl, and

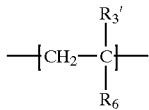

is the 1,2-ethylene radical derived from acrylamide, N,N-dimethyl acrylamide or N-vinylpyrrolidone, wherein, before or after said graft polymerization, a further carbohydrate selected from the group consisting of a galactose, mannose, fucose, galactosamine, N-acetylgalactosamine, N-acetylglucosamine, sialic acid and an oligosaccharide, is enzymatically attached to the acceptor saccharide.

2. A process for the manufacture of an ophthalmic molding comprising the steps:

(a) providing an organic bulk material comprising covalently bound photoinitiator groups on its surface;

(b) co-graft polymerizing onto the bulk material surface:
 (i) one or more different acceptor saccharides comprising an ethylenically unsaturated double bond, to which a further carbohydrate has been enzymatically attached, wherein the further carbohydrate is selected from the group consisting of a galactose, mannose, fucose, galactosamine, N-acetylgalactosamine, N-acetylglucosamine, sialic acid and an oligosaccharide; and
 (ii) a hydrophilic macromonomer of formula

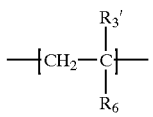

wherein $R_4^*$ is hydrogen or methyl, $A_1$ is —O—$(CH_2)_{2-4}$—, —O—$CH_2$—CH(OH)—$CH_2$— or a radical —O—$(CH_2)_{2-4}$—NH—C(O)—, X is —O— or —NH—, (alk) is $C_2$–$C_4$-alkylene, Q is a monovalent group that is suitable to act as a polymerization chain-reaction terminator, p is an integer from 5 to 50, and $R_3'$ is hydrogen or methyl, and

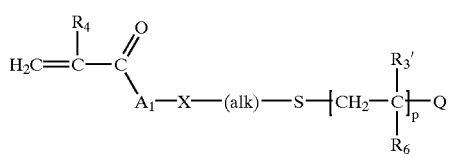

is the 1,2-ethylene radical derived from acrylamide, N,N-dimethyl acrylamide or N-vinylpyrrolidone.

3. An ophthalmic molding according to claim 1, wherein the acceptor saccharides comprising an ethylenically unsaturated double bond are of formula

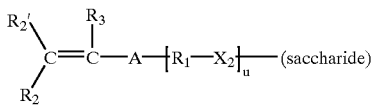

wherein A is a radical of formula

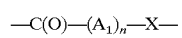   (6a) or

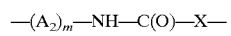   (6b); or

   (6c);

$R_2$ is hydrogen, $C_1$–$C_6$-alkyl or a radical —COOR';

$R_3$, R' and $R_2'$ are each independently of the other hydrogen or $C_1$–$C_6$-alkyl;

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{11}$—NH—C(O)—, wherein $R_{11}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X is a bivalent group —O— or —NR", wherein R" is hydrogen or $C_1$–$C_6$-alkyl;

$R_1$ is a divalent organic radical having from 2 to 30 C-atoms, which may be further substituted;

(saccharide) is the radical of an acceptor saccharide or a derivative thereof;

$X_2$ is a functional group linking $R_1$ to the radical (saccharide); and u is the number 0 or 1.

4. An ophthalmic molding according to claim 3, wherein the radical (saccharide) is the radical of a mono-, di-, tri- or tetrasaccharide or a derivative thereof.

5. An ophthalmic molding according to claim 3, wherein the radical (saccharide) is selected from the group consisting of a lactose, lactobionic acid, N-acetyllactosamine and N-acetylgalactosamine.

6. An ophthalmic molding according to claim 1, wherein the enzymatically attached carbohydrate is sialic acid.

7. An ophthalmic molding according to claim 1, which is a contact lens or a corneal implant.

8. A process for the manufacture of an ophthalmic molding comprising the steps:

(a) providing an organic bulk material comprising covalently bound photoinitiator groups on its surface;

(b) co-graft polymerizing onto the bulk material surface:
(i) one or more different acceptor saccharides comprising an ethylenically unsaturated double bond; and
(ii) a hydrophilic macromonomer of formula

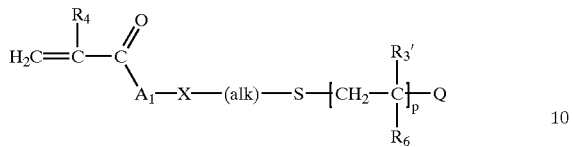

wherein $R_4^*$ is hydrogen or methyl, $A_1$ is —O—$(CH_2)_{2-4}$—, —O—$CH_2$—CH(OH)—$CH_2$— or a radical —O—$(CH_2)_{2-4}$—NH—C(O)—, X is —O— or —NH—, (alk) is $C_2$-$C_4$-alkylene, Q is a monovalent group that is suitable to act as a polymerization chain-reaction terminator, p is an integer from 5 to 50, and $R_3'$ is hydrogen or methyl, and

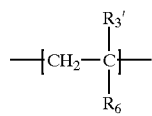

is the 1,2-ethylene radical derived from acrylamide, N,N-dimethyl acrylamide or N-vinylpyrrolidone; and
(c) enzymatically attaching a further carbohydrate to the acceptor saccharide,
wherein the further carbohydrate is selected from the group consisting of a galactose, mannose, fucose, galactosamine, N-acetylgalactosamine, N-acetylglucosamine, sialic acid and an oligosaccharide.

* * * * *